United States Patent
Duerig et al.

(10) Patent No.: US 12,037,672 B2
(45) Date of Patent: Jul. 16, 2024

(54) MATERIALS HAVING SUPERELASTIC PROPERTIES INCLUDING RELATED METHODS OF FABRICATION AND DESIGN FOR MEDICAL DEVICES

(71) Applicant: CONFLUENT MEDICAL TECHNOLOGIES, INC., Fremont, CA (US)

(72) Inventors: Thomas Duerig, Fremont, CA (US); Ali Shamimi, Oakland, CA (US); Craig Bonsignore, Pleasanton, CA (US)

(73) Assignee: Confluent Medical Technologies, Inc., Fremont, CA (US)

(*) Notice: Subject to any disclaimer, the term of this patent is extended or adjusted under 35 U.S.C. 154(b) by 174 days.

(21) Appl. No.: 16/343,653

(22) PCT Filed: Oct. 23, 2017

(86) PCT No.: PCT/US2017/057888
§ 371 (c)(1),
(2) Date: Apr. 19, 2019

(87) PCT Pub. No.: WO2018/076010
PCT Pub. Date: Apr. 26, 2018

(65) Prior Publication Data
US 2019/0276921 A1    Sep. 12, 2019

Related U.S. Application Data

(60) Provisional application No. 62/411,513, filed on Oct. 21, 2016.

(51) Int. Cl.
*C22F 1/10*    (2006.01)
*A61L 27/06*    (2006.01)
(Continued)

(52) U.S. Cl.
CPC ............. *C22F 1/10* (2013.01); *A61L 27/06* (2013.01); *A61L 29/02* (2013.01); *A61L 29/14* (2013.01);
(Continued)

(58) Field of Classification Search
None
See application file for complete search history.

(56) References Cited

U.S. PATENT DOCUMENTS 5,067,957 A    11/1991  Jervis
5,958,159 A     9/1999  Prandi
(Continued)

FOREIGN PATENT DOCUMENTS

CN    107475652 A  * 12/2017
WO    WO97/049353 A1  12/1997
WO    WO2004/092431 A1  10/2004

OTHER PUBLICATIONS

English Translation of CN 107475652 (originally published Dec. 15, 2017), obtained from PE2E search.*
(Continued)

*Primary Examiner* — George Wyszomierski
(74) *Attorney, Agent, or Firm* — Shay Glenn LLP

(57) ABSTRACT

There are super elastic NiTi materials for use as medical components, especially implantable medical components, and methods of fabricating such components to have desired R-phase characteristics in-vivo. Additionally, there are methods of processing a TiNi material to produce an implantable medical component by cold or warm working the TiNi material at least 15%; aging the cold or warm worked TiNi material under stress at between 300-700° C.; and further aging the TiNi material below 300° C. to produce desired R-phase characteristics. Additionally, there are methods of processing a TiNi material to produce a medical
(Continued)

component by processing the TiNi material to produce a medical component that has a stress free M*s below a normal body temperature. Additionally, a TiNi material is used to produce a super elastic medical component from a tube, a sheet, a wire or a strip to have a stress free M*s below a normal body temperature.

9 Claims, 36 Drawing Sheets

(51) Int. Cl.
| A61L 29/02 | (2006.01) |
| A61L 29/14 | (2006.01) |
| A61L 31/02 | (2006.01) |
| A61L 31/14 | (2006.01) |
| B32B 5/18 | (2006.01) |
| C22C 1/04 | (2023.01) |
| C22C 14/00 | (2006.01) |
| C22C 19/00 | (2006.01) |
| C22C 32/00 | (2006.01) |
| C22F 1/00 | (2006.01) |

(52) U.S. Cl.
CPC ............ *A61L 31/022* (2013.01); *A61L 31/14* (2013.01); *B32B 5/18* (2013.01); *C22C 1/04* (2013.01); *C22C 14/00* (2013.01); *C22C 19/00* (2013.01); *C22C 19/007* (2013.01); *C22C 32/00* (2013.01); *C22F 1/006* (2013.01); *A61L 2400/16* (2013.01)

(56) References Cited

U.S. PATENT DOCUMENTS

| 2004/0014253 | A1 | 1/2004 | Gupta et al. |
| 2004/0187980 | A1* | 9/2004 | Jung ................ C22C 19/007 148/563 |
| 2004/0216816 | A1 | 11/2004 | Wojcik |
| 2008/0215131 | A1* | 9/2008 | Magnuson ............... C22F 1/10 623/1.12 |
| 2009/0139614 | A1 | 6/2009 | Magnuson et al. |
| 2009/0162243 | A1 | 6/2009 | Diamant et al. |
| 2010/0016952 | A1* | 1/2010 | Prokoshkin ........... A61L 31/022 623/1.18 |
| 2011/0106237 | A1 | 5/2011 | Bonsignore et al. |
| 2011/0253525 | A1 | 10/2011 | Johnson et al. |
| 2013/0166010 | A1* | 6/2013 | Vad ........................ A61F 2/89 623/1.2 |
| 2013/0205567 | A1 | 8/2013 | Wong et al. |
| 2014/0249614 | A1* | 9/2014 | Levi ......................... A61F 2/07 623/1.11 |
| 2015/0230843 | A1* | 8/2015 | Palmer ................ A61B 17/7291 606/331 |
| 2016/0243289 | A1 | 8/2016 | Yamauchi et al. |
| 2018/0311406 | A1* | 11/2018 | Francis ................ A61L 27/06 |

OTHER PUBLICATIONS

Kim et al; Effect of nano-scaled precipitates on shape memory behavior of Ti-50.9at.%Ni alloy; Acta Materialia; 53(17); pp. 4545-4554; Oct. 1, 2005 <https://doi.org/10.1016/j.actamat.2005.06.009>.

Miyazaki et al.; Transformation pseudoelasticity and deformation behavior in a Ti-50.6 at% Ni alloy; Scripta Metallurgica; 15(3): pp. 287-292; Mar. 1, 1981.

Pourbabak et al; Ni cluster formation in low temperature annealed Ni50.6Ti49.4; Funcational Materials, Letters, 10(1); 1740005, Feb. 13, 2017 <https://doi.org/10.1142/S1793604717400057>.

Zheng et al; Effect of ageing treatment on the transformation behaviour of TiR50.9 at.% Ni alloy; Acta Materialia; 56(4); 736-745; (Author Manuscript); Feb. 1, 2008.

Standard AS; Standard test method for transformation temperature of nickel-titanium alloys by thermal analysis; ASTM Standard;5; pp. 1-4, 2004.

ASTM F2005-05, Standard Terminology for Nickel-Titanium Shape Memory Alloys, ASTM International, West Conshohocken, PA, 2015.

* cited by examiner

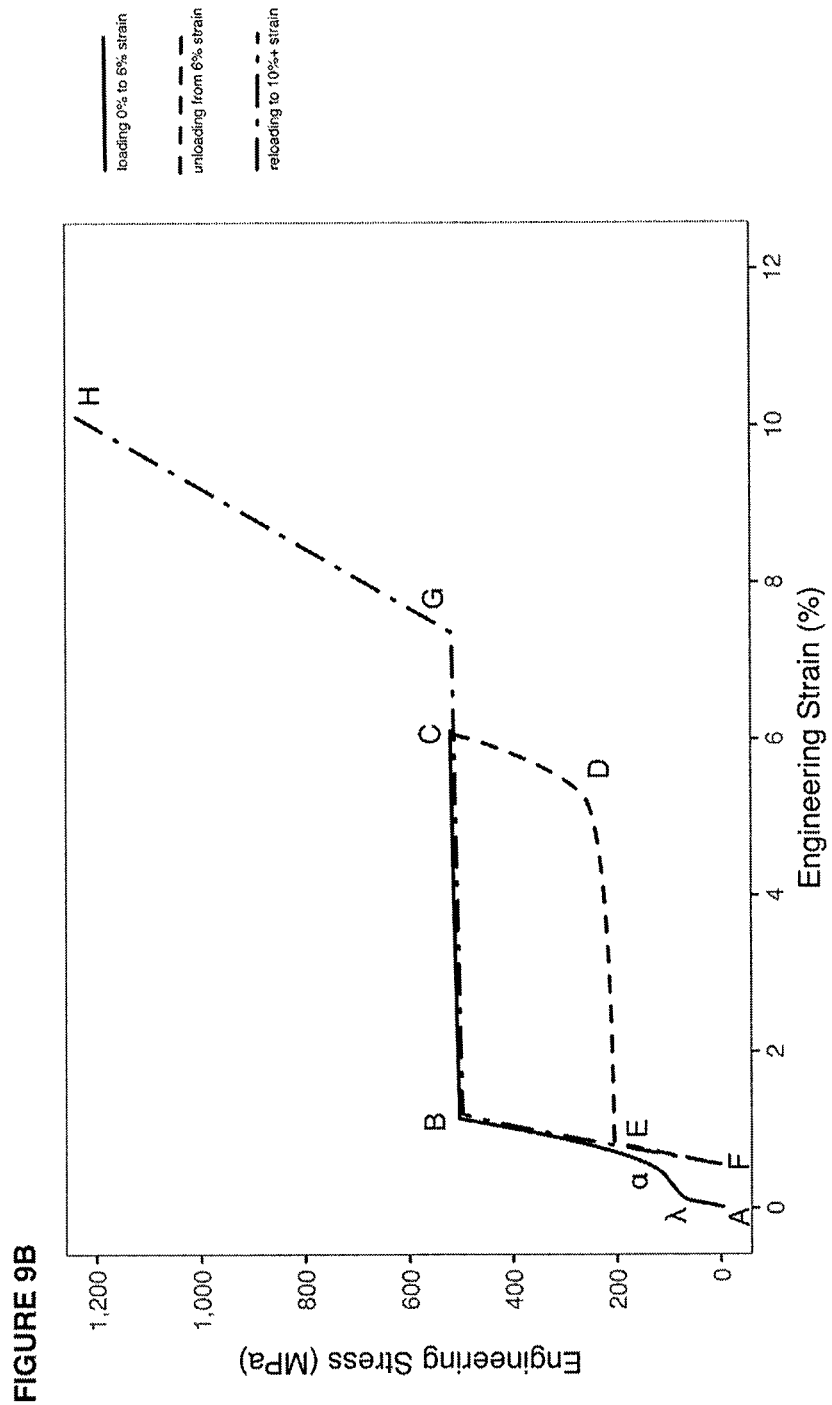

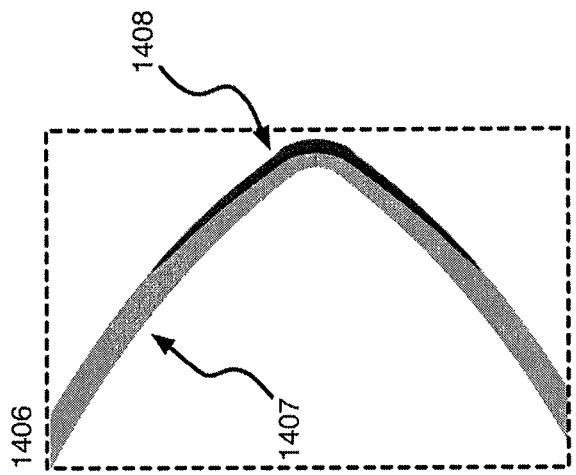
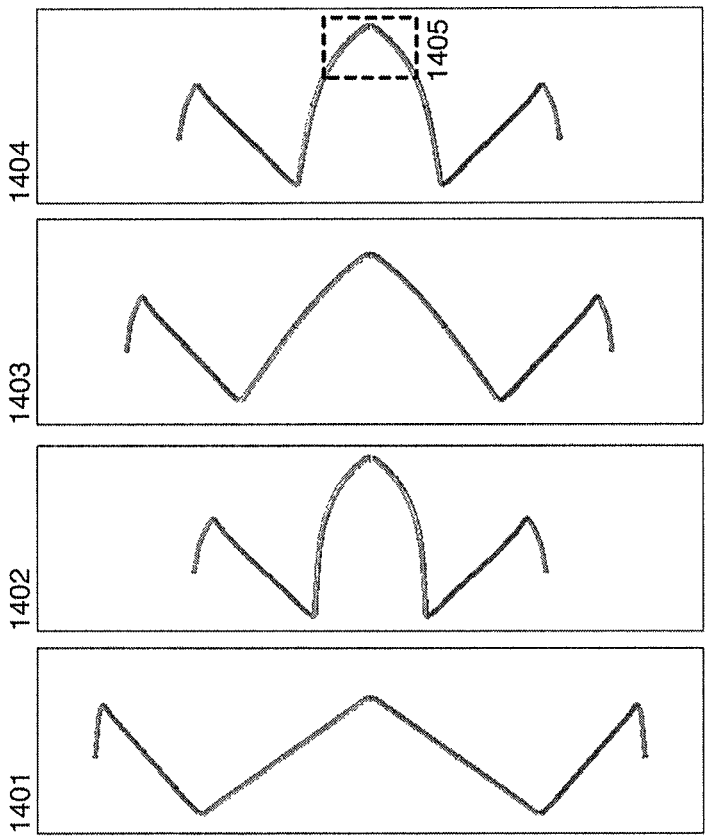
FIG. 14E
FIG. 14D
FIG. 14C
FIG. 14B
FIG. 14A

MATERIALS HAVING SUPERELASTIC PROPERTIES INCLUDING RELATED METHODS OF FABRICATION AND DESIGN FOR MEDICAL DEVICES

CROSS REFERENCE TO RELATED APPLICATIONS

This application claims priority to U.S. Provisional Patent Application No. 62/411,513, filed Oct. 21, 2016 and titled "MATERIALS HAVING SUPERELASTIC PROPERTIES INCLUDING RELATED METHODS OF FABRICATION AND DESIGN FOR MEDICAL DEVICES," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The various embodiments described herein relate to superelastic NiTi materials for use as medical components, especially implantable medical components and methods of fabricating such components to have improved R-phase characteristics in-vivo.

BACKGROUND

It is commonly assumed that NiTi, or Nitinol, exists in either the B19' Martensite ("Martensite") or B2 Austenite ("Austenite") phase, the former being stable at lower temperatures and higher stresses, and the latter at higher temperatures and lower stresses—thus one can either thermally induce or stress induce Martensite from Austenite. Austenite is a cubic phase, and Martensite is a much more complex monoclinic structure that has the ability to change shape through a process called "twinning". The fact that Martensite is crystallographically complex is what makes it more stable at low temperatures (lower entropy), and its ability to change shape is what makes it the more stable phase at high stresses. For the same reasons, ice is more stable than liquid water at low temperatures, and greater stresses stabilize liquid over ice because liquid is able to change shape easily whilst ice is not.

The term $A_f$ is in common use to signify the temperature at which an alloy becomes "fully" Austenitic during heating. We use the term "fully" here with the understanding that it is common to find traces of Martensite well past what industry defines as the "finish" of the transformation. Here we follow the commonly used "tangent construction" to define $A_p$ as will be demonstrated later. This definition and use is common in industry and supported by ASTM standards[1].

[1] See ASTM F 2004-05 *Standard Test Method for Transformation Temperature of Nickel-Titanium Alloys by Thermal Analysis*, and ASTM F 2005-05 *Standard Terminology for Nickel-Titanium Shape Memory Alloys*

While Austenite is the stable phase just above the $A_f$ temperature, the application of a stress can stabilize the Martensitic phase, and once it is in its Martensitic condition, the alloy can easily change shape per the aforementioned twinning mechanism. Removing that load returns stability to Austenite and the original shape is recovered, a well-known process called superelasticity, or pseudoelasticity as described by Jervis and others[2].

[2] See, for example, J Jervis, U.S. Pat. No. 5,067,957 (1991) Method of inserting medical devices incorporating SIM alloy Elements and its antecedents, or S Miyazaki et al., Transformation Pseudoelasticity and Deformation Behavior in a Ti-50.8 at % Ni Alloy, Scripta Metall. 15, (1981) page 287.

Despite this conventional understanding of superelasticity and its prevalent use in the existing commercial designs, there remains a need for improvement in the properties and performance characteristics of materials that exhibit superelastic or pseudoelastic properties.

SUMMARY OF THE DISCLOSURE

In general, in one embodiment, a method of processing a TiNi material to produce an implantable medical component includes processing the TiNi material to produce a medical component, wherein the medical component has a stress free $M^*_s$ below a normal body temperature.

This and other embodiments can include one or more of the following features. The medical component can have a stress free $M^*_p$ below a normal body temperature. The medical component can have a stress free $M^*_f$ below a normal body temperature. In use in-vivo the medical component can contain at least some R-phase. The medical component can have an R-phase that is stress induced below the lower plateau stress. A critical region of the medical component can be substantially R-phase and Martensite. During a duty cycle applied during in-vivo use the medical component can alternate between Martensite and R-phase. The medical component can have a stress free $A_f$ above body temperature. The medical component can have a stress free $A_p$ above body temperature. The medical component can have a stress free $A_s$ above body temperature. Temperature separation of the stress free $R^*_p$ and $M^*_p$ can be at least 30° C. Temperature separation of the stress free $R_p$ and $M_p$ can be at least 100° C. The TiNi material can be a binary composition comprising substantially only Ti and Ni. The Ni atomic percentage can be 50.5-51.5%. The TiNi material can be a tertiary composition including Ti and Ni and at least one other element. The at least one other element can be a Martensite suppressive material. The at least one other element can be Co, Al, Fe, Cr. The at least one element can be Co within the range of 0.01 to 3%. The at least one element can be Al within the range of 0.01 to 2%. The at least one element can be Fe within the range of 0.01 to 3%. The at least one element can be Cr within the range of 0.1 to 2%. The TiNi material can include more than 50% atomic volume Ni, from 0.1 to 3% of a Titanium substitution material with remaining composition comprising Ti. The Titanium substitution material can be one of Hf, Zr, or Nb alone or in any combination.

In general, in one embodiment, a method of processing a TiNi material to produce an implantable medical component includes cold or warm working the TiNi material at least 15%, aging the cold or warm worked TiNi material under stress at between 300° C.-700° C., and further aging the TiNi material below 300° C. to produce desired R-phase characteristics.

This and other embodiments can include one or more of the following features. The further aging step can be performed under stress conditions or under stress free conditions. The step of warm or cold working can be 20-50%, and at least 15%. The step of aging after the warm or cold working can be aging between 500° C.-580° C. The further aging step can be between 150° C.-250° C. The final UTS of a NiTi component can be at least 1,000 MPa. The step of aging the cold or warm worked TiNi material can be repeated at least once. The NiTi material can be a tube or sheet and a method of laser cutting the NiTi tube or sheet can be performed after performing at least one step of aging or cold worked NiTi material. The NiTi material can be a wire or a strip and a method of bending the wire or strip can be performed after performing at least one step of aging or cold worked NiTi material. The NiTi material can be a wire or a strip and the step of aging the cold or warm worked TiNi material under stress at between 300° C.-700° C. can include bending the wire or the strip.

In general, in one embodiment, a superelastic medical component includes a tube, a sheet, a wire or a strip of a TiNi material formed into the super elastic medical component and having a stress free $M^*_s$ below a normal body temperature.

This and other embodiments can include one or more of the following features. The medical component can have a stress free $M^*_p$ below a normal body temperature. The medical component can have a stress free $M^*_f$ below a normal body temperature. In use in-vivo the medical component can contain at least some R-phase. The medical component can have an R-phase that is stress induced below the lower plateau stress. The medical component can have a stress free $A_f$ above body temperature. The medical component can have a stress free $A_p$ above body temperature. The medical component can have a stress free $A_s$ above body temperature.

Any of the above variations of a medical component described above can be adapted and configured for use in the field of interventional cardiology and neuroradiology. The medical component can be one of an angioplasty balloon shaft, a stent, a stent graft, a coil or a component of a delivery system. The medical component can be adapted and configured for use in the field of cardiovascular surgery, general surgery or laparoscopic surgery. The medical component can be one of a valve sizer, a tissue retractor, a heart valve, a stent for use in the arterial system, a stent for use in the venous system, an instrument or component of a specimen retrieval system. The medical component can be adapted and configured for use in the field of orthopedic surgery, spine surgery or sports medicine. The medical component can be one of a bone staple, a bone screw, a scoliosis rod, a spinal fixation rod, a suture retriever or a k-wire. The medical component can be adapted and configured for use in the field of urology, gastrointestinal health, otolaryngology, obstetrics or gynecology. The medical component can be one of a snare, a grasper, an esophageal stent, a biliary stent, a stent for use within the gut, or a sinus implant. The medical component can be adapted and configured for use in the field of dentistry or orthodontics. The medical component can be one of an arch wire, an orthodontic clip or a component used in a repair of the mouth. The medical component can be adapted and configured for use as a diagnostic catheter, a therapeutic catheter, a stent, a needle, a wire localizer, an orthodontic arch wire, a lead for an implantable stimulation component or a component of an implantable drug delivery system.

BRIEF DESCRIPTION OF THE DRAWINGS

FIG. 9B is a variant of 9A corresponding to the material shown in FIG. 8B, beginning with Austenite, stress-inducing R-phase, proceeding to Martensite, reverting to R-phase upon unloading, and not fully recovering to the original Austenite configuration.

FIGS. 14A-14E illustrate different aspects of several critical regions in an example component formed from wire or strip.

(FIGS. 16A and 16D), 150° C. (FIGS. 16B and 16E) and 200° C. (FIGS. 16C and 16F). The traces in FIGS. 16A, 16B and 16C indicate the forward exothermic direction (cooling) and those in FIGS. 16D, 16E and 16F indicate the reverse endothermic direction (heating).

(FIGS. 20A and 20E), 150° C. (FIGS. 20B and 20F), 200° C. (FIGS. 20C and 20G) and 250° C. (FIGS. 20D and 20H).

(FIG. 24A), 150° C. (FIG. 24B), 200° C. (FIG. 24C) and 250° C. (FIG. 24D).

with aging and R-phase stabilization under various conditions.

Figure 29:
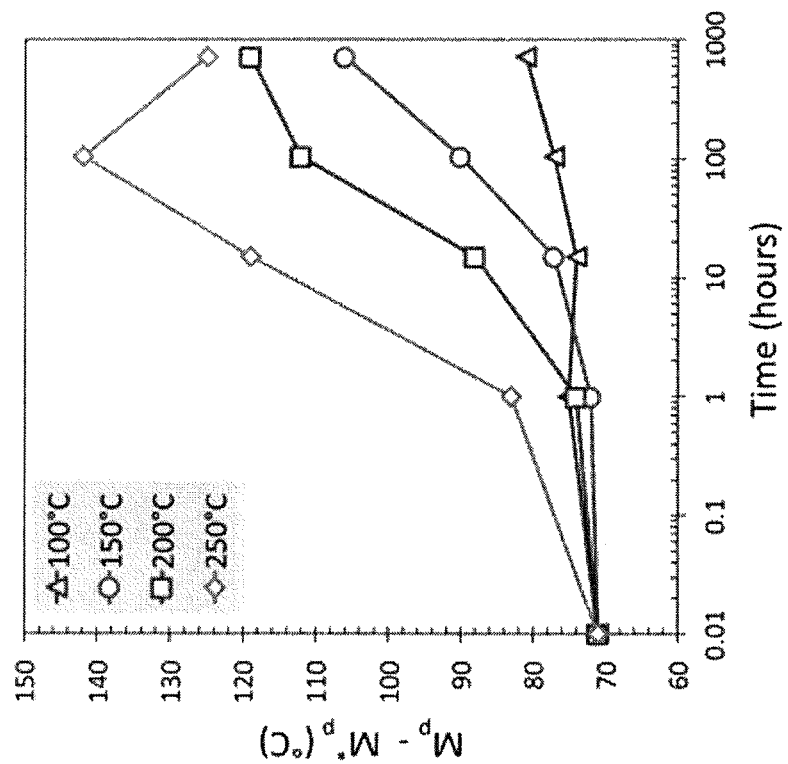

FIG. 29 illustrates the evolution of hysteresis with aging temperature and time for various conditions.

DETAILED DESCRIPTION

As further detailed in the explanation that follows, we define superelasticity as meaning that there is some degree of deformation, after which unloading will result in a stress plateau, often referred to as an Unloading Plateau, or Lower Plateau. We further define "plateau" as meaning that the slope exhibits an inflection point (the slope of the stress-strain curve upon unloading exhibits a minimum). Typically, clear, well-formed plateaus would be exhibited after between 3% and 10% strains, but this is not a limitation—poorly formed unloading plateaus that exhibit an inflection point may be exhibited after any deformation above 1%, even up to or in excess of 14% tensile deformation. In ideal cases, superelastic behavior results in less than 1% residual strain after deformations of 6%, but that too is not a limitation.

Figure 1:
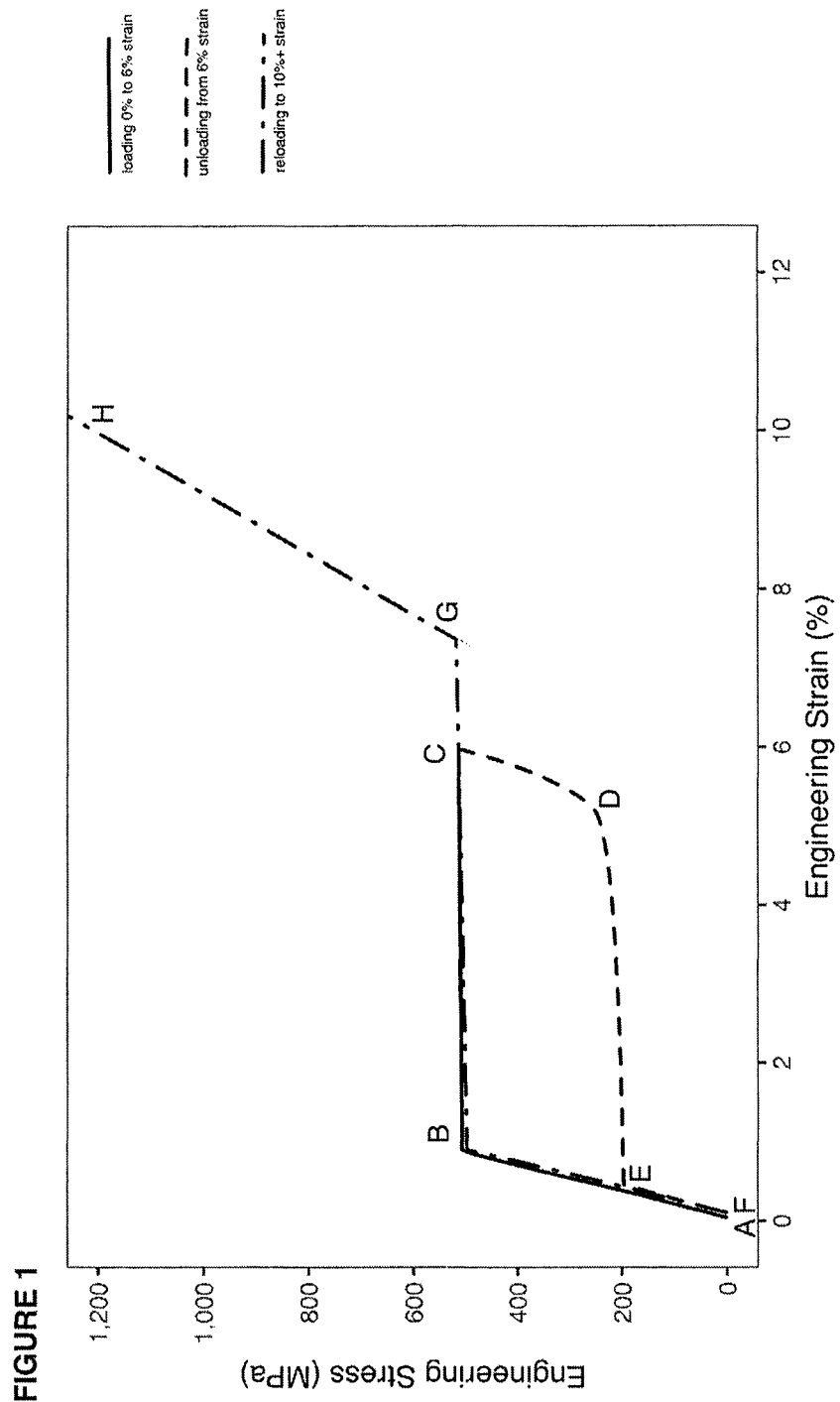
FIG. 1 is a conventional superelastic stress-strain diagram, illustrating the physical characteristics common to conventional superelasticity, such as upper plateau stress (UPS), lower plateau stress (LPS). In this figure, the specimen experiences loading in Austenite, stress induced transformation to Martensite, reversion to Austenite, and reloading to Martensite

An example of such a classic Austenite-Martensite superelastic stress strain curve measured above $A_f$ is shown in FIG. 1, a conventional superelastic stress-strain diagram for a specimen loaded and unloaded in uniaxial tension at a constant temperature of 37° C. Beginning at point A, the specimen is fully Austenitic, following the elastic modulus of B2 Austenite until point B. From point B to C, B2 Austenite transforms to B19' Martensite. The B-C region (also continuing to G, described later) is known as the upper plateau, or loading plateau. Moving from B to C, the volume fraction of Martensite increases. Volume fraction of Martensite means the volume of Martensite relative to the volume of material under stress. At point C, 6% strain, the specimen is partially transformed to Martensite, meaning that a portion of the volume has transformed to Martensite. Unloading from point C, the transformed B19' Martensite reverts to B2 Austenite from point D to E. The D-E region is known as the lower plateau, or unloading plateau. The specimen is essentially fully Austenitic at point E, and follows the previously observed austenite elastic modulus from E to F. The specimen fully recovers to its original configuration at point F, which is preferably essentially coincident with point A. Reloading from point F, the specimen retraces the original path from A to B. From point B to G, the B2 Austenite fully transforms to B19' Martensite, and is largely fully martensitic at point G. At this point G, the effective volume fraction of Martensite is nearly or approximately unity. Loading from G to H, the specimen is loaded in its Martensitic phase. Continued loading in excess of the elastic limits of Martensite will result in plastic deformation of the material. Importantly, it is recognized that point G is not the complete finish of the stress induced transformation to Martensite, but rather some transformation continues beyond point G, just as some plasticity may occur prior to arriving at point H. Point G merely marks the stress and strain where the transformation is substantially complete, which may mean more than 85% complete. The difference between actual vs. effective volume fraction of Martensite (e.g. 85% vs. unity) may be influenced by polycrystalline characteristics of the specific material: grain size, orientation, and variability, especially as related to the direction of the applied stress. Grains oriented favorably with respect to the applied stress may approach a Martensite volume fraction of unity, while unfavorably oriented grains may transform to a significantly less degree. The tensile test of FIG. 1 represents the effective response of the polycrystalline material for an applied, while other analytical methods, such as x-ray diffraction, are suitable to resolve the actual degree of transformation at individual grains. The structure is primarily austenite in the A-B and E-F regions, while residual R-phase, B19' Martensite, or plastified material may also be present in relatively small but detectable quantities.

In many Nitinol alloys and conditions, particularly in cold worked and/or aged Ni-rich alloys, a third phase called the R-phase appears under certain conditions, inserting itself between Austenite and Martensite. The R-phase is rhombohedral in nature, and is intermediate to Austenite and Martensite in entropy. Like Martensite, the R-phase has the ability to change shape, albeit to a much lesser extent. In fact, the R-phase is also a martensitic phase, though for clarity here we refer to it as the R-phase and reserve the capitalized term "Martensite" to mean the monoclinic structure (also known as B19'). Because the R-phase is of lower entropy than Martensite and is less accommodating to applied stresses, its stability relies heavily on the fact that it is much more easily formed than Martensite—it requires substantially less supercooling.

Figure 2:
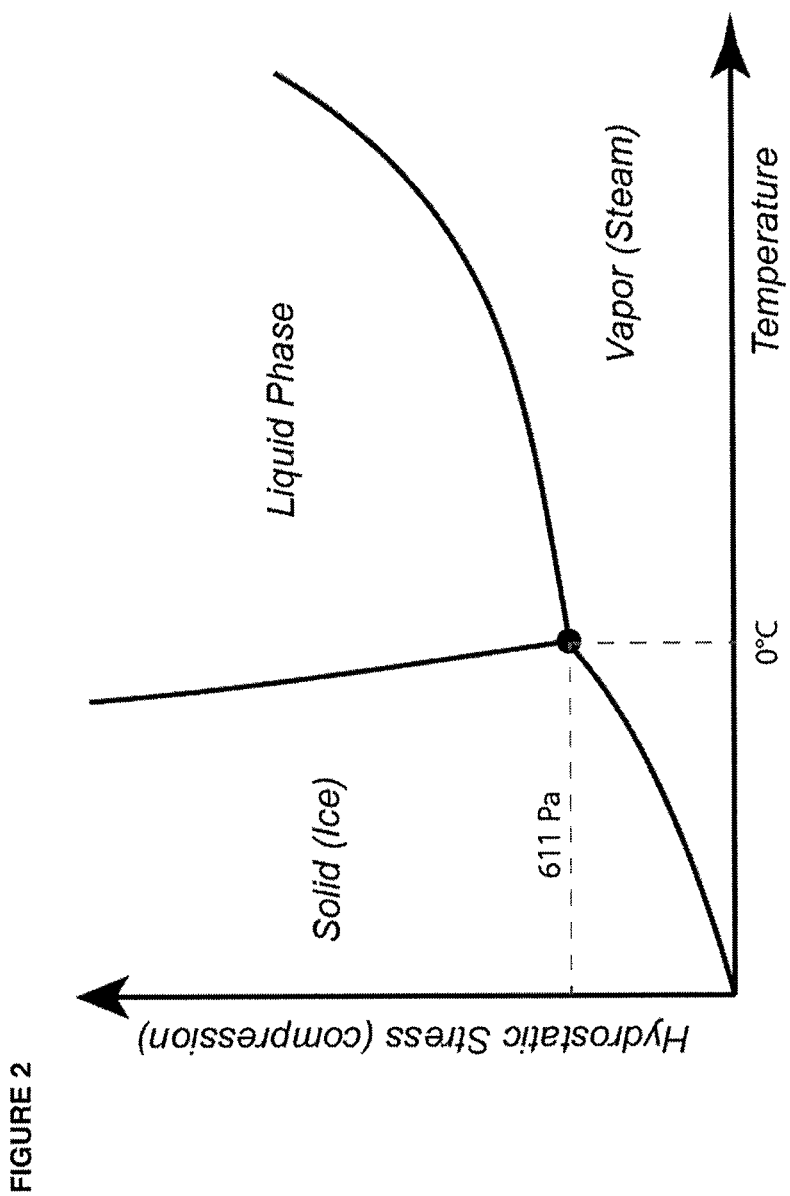
FIG. 2 is phase diagram for simple water indicating that cooling of steam can result in the formation of ice or of liquid water, depending upon the stress (pressure). These same principles apply to Nitinol.

To help understand the interaction between the M, R and A phases, it may be useful to imagine the water system, with its three common phases, ice, liquid water, and steam. As illustrated in FIG. 2, the liquid phases can, under certain circumstances, be intermediate to ice and steam. With no stress (pressure), however, ice transforms directly to steam, without need for the intermediate liquid phase.

Most medical devices exhibit the R-phase under certain stress and temperature conditions. Just as the phase-temperature (P-T) phase diagram for water (FIG. 2) can be used to map out the conditions under which water's intermediate phase (liquid water) exists, one can develop stress-temperature diagrams for NiTi alloys that map precisely when the R-phase and Martensite form upon cooling (see, for example, FIG. 3A). Note that this figures governs only the formation of Martensite from either R-phase or Austenite—the reversion of Martensite occurs after a hysteresis, and results in a figure such as FIG. 3B.

Figure 3A:
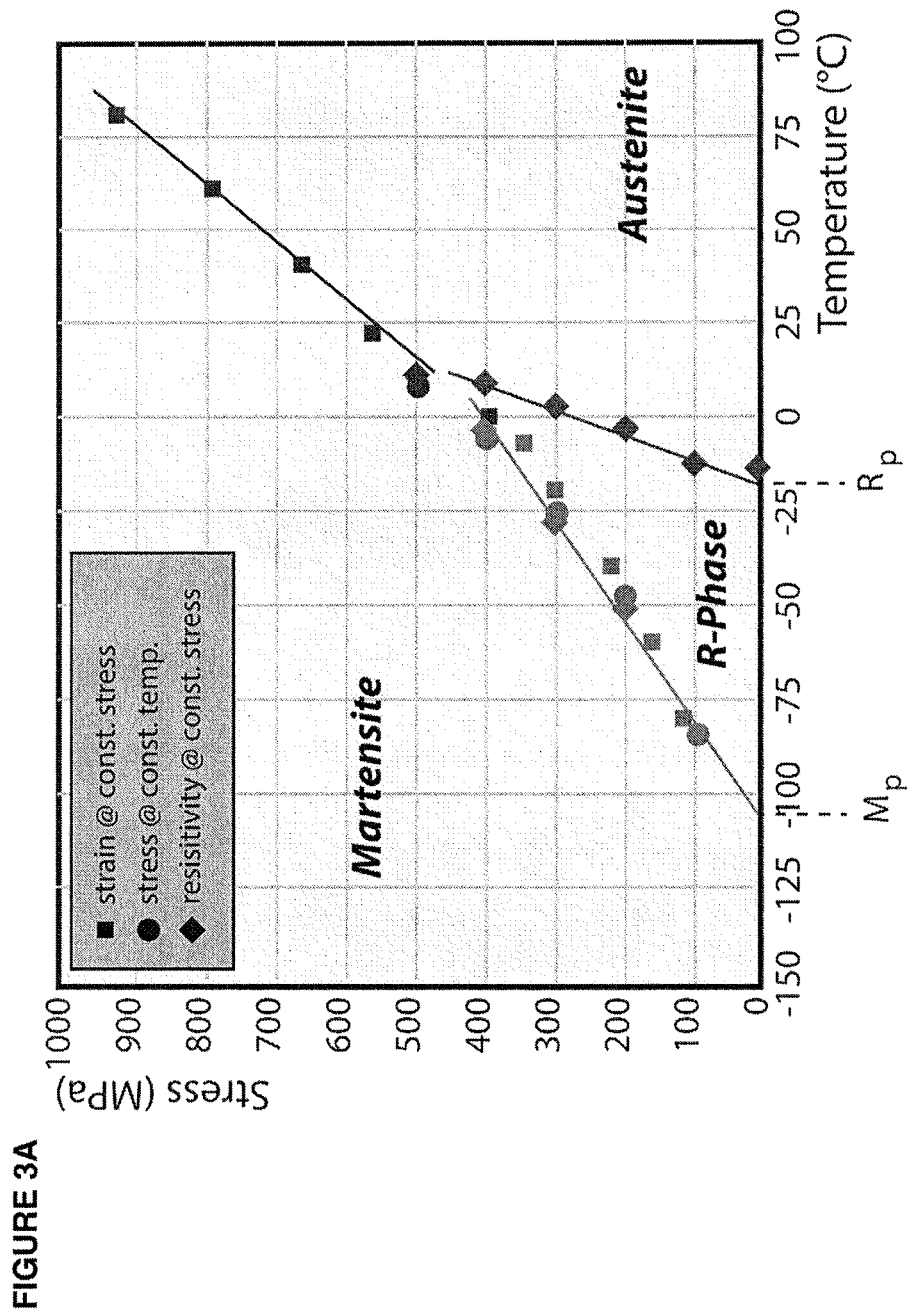
FIG. 3A is a "forward" phase diagram analogous to FIG. 2 shown for a conventional superelastic material as might be used in a medical device. "Forward" means that one is moving toward Martensite by any combination of cooling or stressing (moving from the lower right to upper right). Rp indicates the temperature at which formation of R is most rapid, and Mp indicates the temperature at which formation of M is most rapid. Note that at body temperature of 37° C., the R-phase is not present.
Figure 3B:
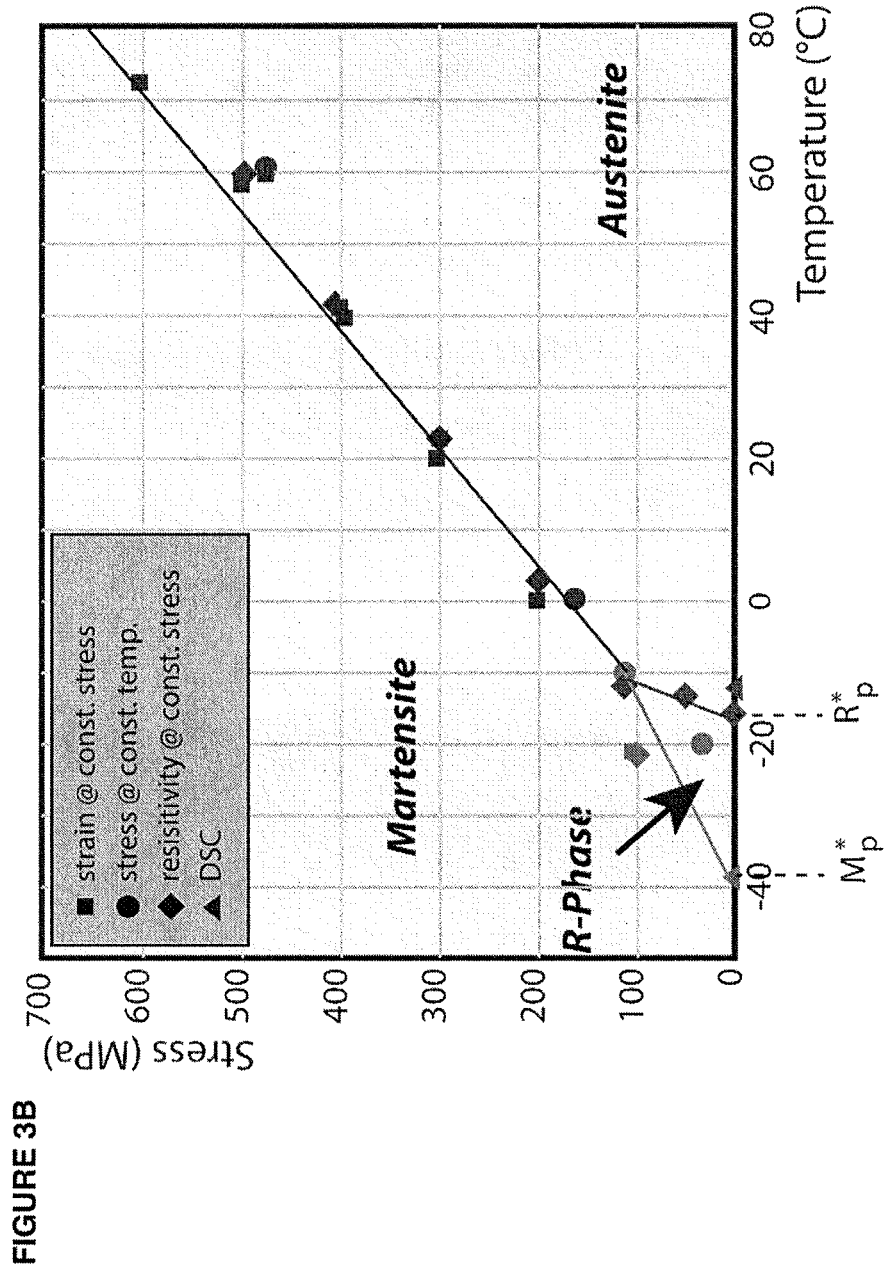
FIG. 3B is a "reverse" phase diagram analogous to FIG. 2 shown for a conventional superelastic material as might be used in a medical device. "Reverse" means that one is moving away from Martensite by any combination of heating or unstressing (moving from the upper left to lower right). $R^*_p$ indicates the temperature at which the dissolution of R is most rapid at zero stress, and $M^*_p$ indicates the temperature at which reversion of M is most rapid at zero stress.
Figure 6A:
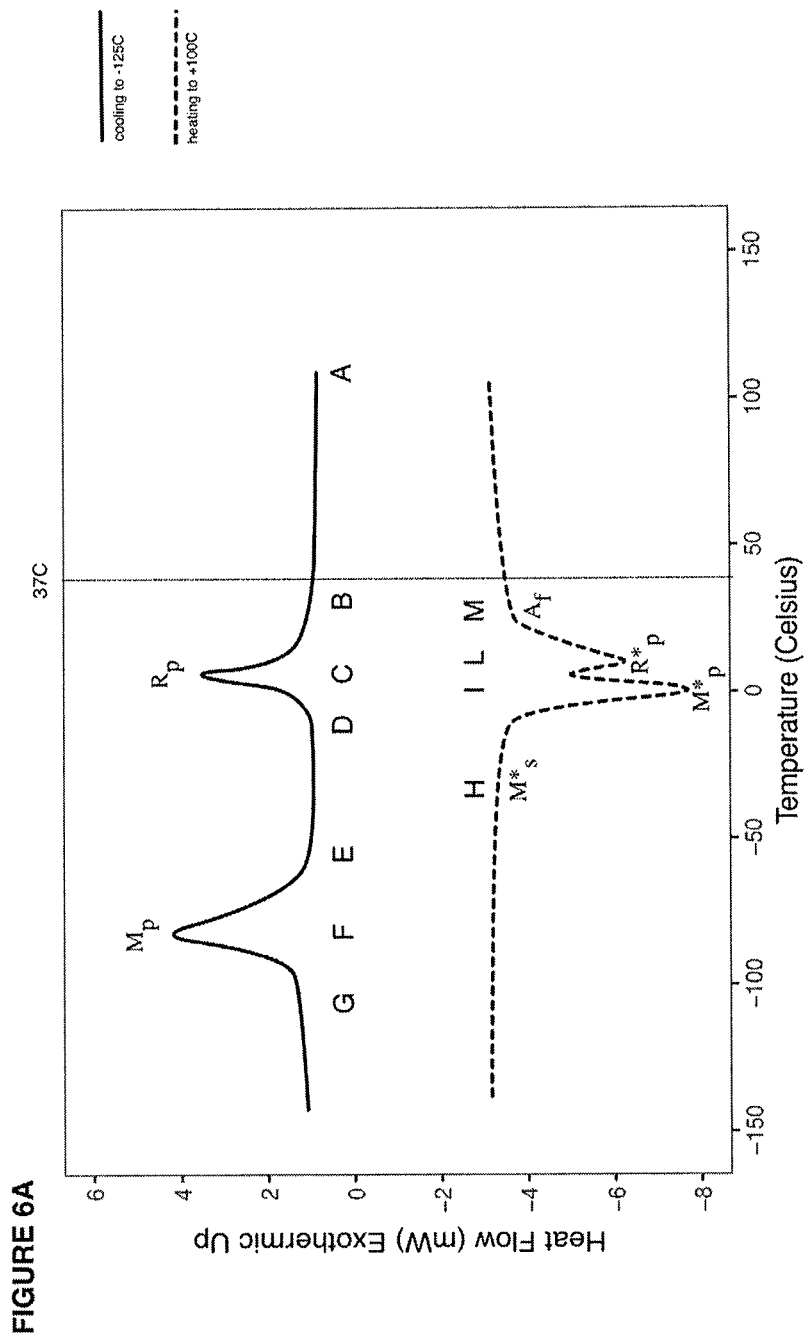
FIG. 6A is a typical Differential Scanning calorimetry (DSC) curve for a conventional superelastic medical device with key temperatures indicated. DSC is often used to determine the zero-load (stress-free) transformation temperatures indicated on FIG. 4.

Noted on the horizontal axis of FIGS. 3A and 3B are key transformation temperatures: $R_p$, $M_p$, $R^*_p$ and $M^*_p$. Here the "*" indicates the reversion of that phase (R indicating the R-phase and or M the monoclinic Martensite phase), and the "p" signifies that the temperature at which transformation is most rapid. It is understood that all these transformation must start before they become most rapid, and finish after that point, thus it is also common to use subscripts "s" and "f" to indicate the temperatures at which these transformations start and finish. For example, $R_s$ would mean the beginning of a transformation to the R-phase, and $M^*_f$ would mean the completion of the reversion of Martensite. The term "$A_f$" meaning the finish of the transformation to Austenite, may be synonymous with $M^*_f$ if Martensite reverts directly to Austenite without the intermediate R-phase, or it might be synonymous with $R^*_f$ if the R-phase is intermediate to Martensite and Austenite. These transformation temperatures can be measured using a variety of different tools, such as x-ray diffraction, mechanical deformation, resistivity, etc. Perhaps of greatest convenience, however, is to use Differential Scanning calorimetry (DSC) as shown in FIG. 6A. This particular curve corresponds to the previous art with respect to superelastic medical devices with an $A_f$ temperature below body temperature—in other words, this wire would be "fully" Austenitic at body temperature and exhibit classical superelasticity. Note that $R^*_p$ and $M^*_p$ temperatures marked on this figure differ in terminology to the terminology used in the ASTM standards referenced in the background section. The reason to deviate from the former terminology is to avoid confusion when Martensite reverts to R-phase rather than Austenite. In the former terminology, the term "$R'_p$" would be used instead of $M^*_p$ and "$A_f$" is used instead of $R^*_p$.

Conventional methods of measuring and interpreting transition temperatures may be insufficient to accurately resolve the Martensite formation peak, differentiate the Martensite reversion peak from the R-phase reversion peak, or identify the start or finish of these transitions. Improved methods are described in detail in "The Measurement and Interpretation of Transformation Temperatures in Nitinol", authored by Tom Duerig, Alan Pelton, and Kaushik Bhattacharya, submitted 5 Oct. 2017, and accepted for publication in the Journal Shape Memory and Superelasticity. This document is incorporated herein by reference.

Figure 4:
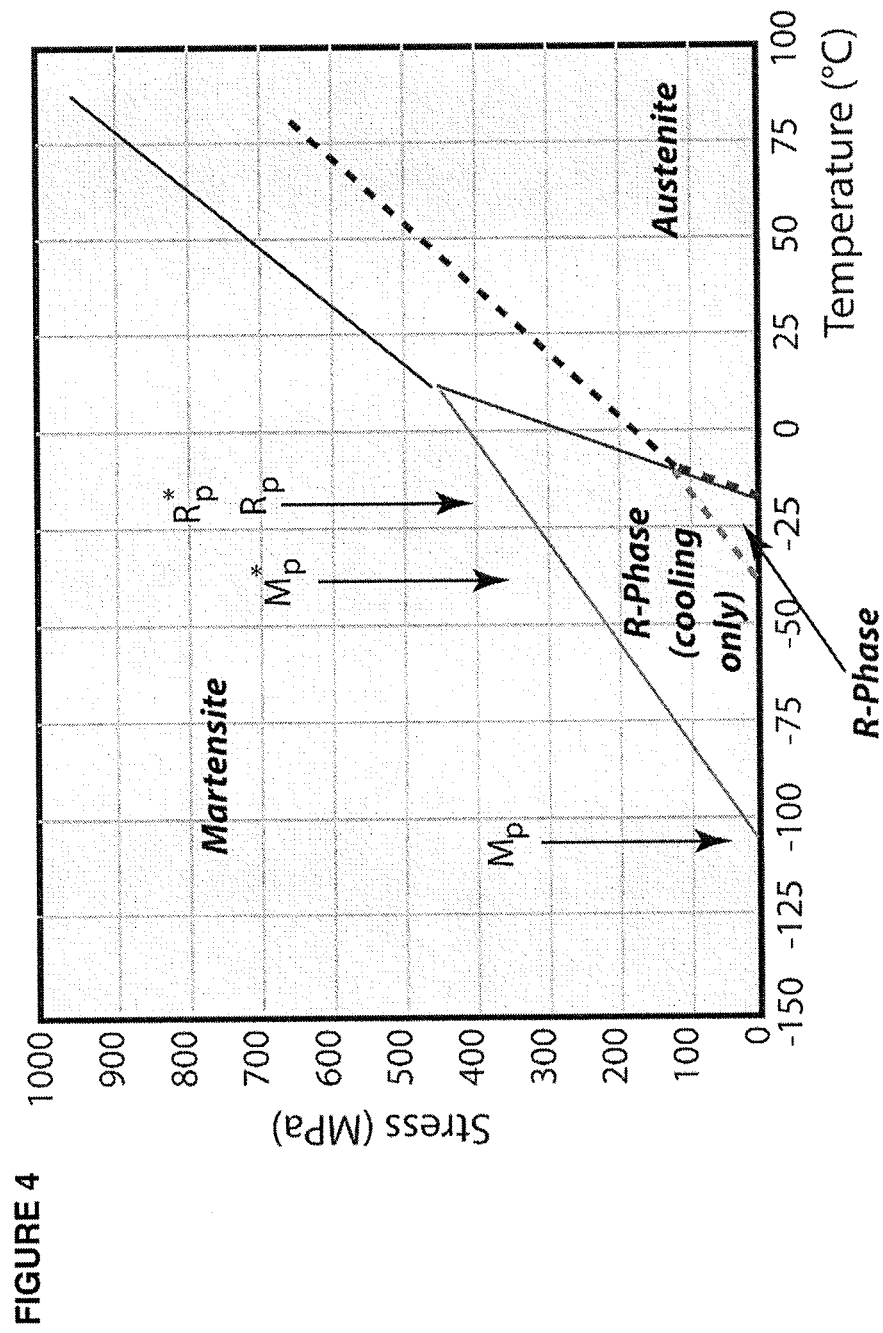
FIG. 4 shows an entire phase diagram for a typical superelastic material as might be used in a conventional superelastic device, with the four key transformations indicated. Note that the stability range of the R-phase is much greater upon cooling (or stressing) than upon heating (or unloading).
Figure 5:
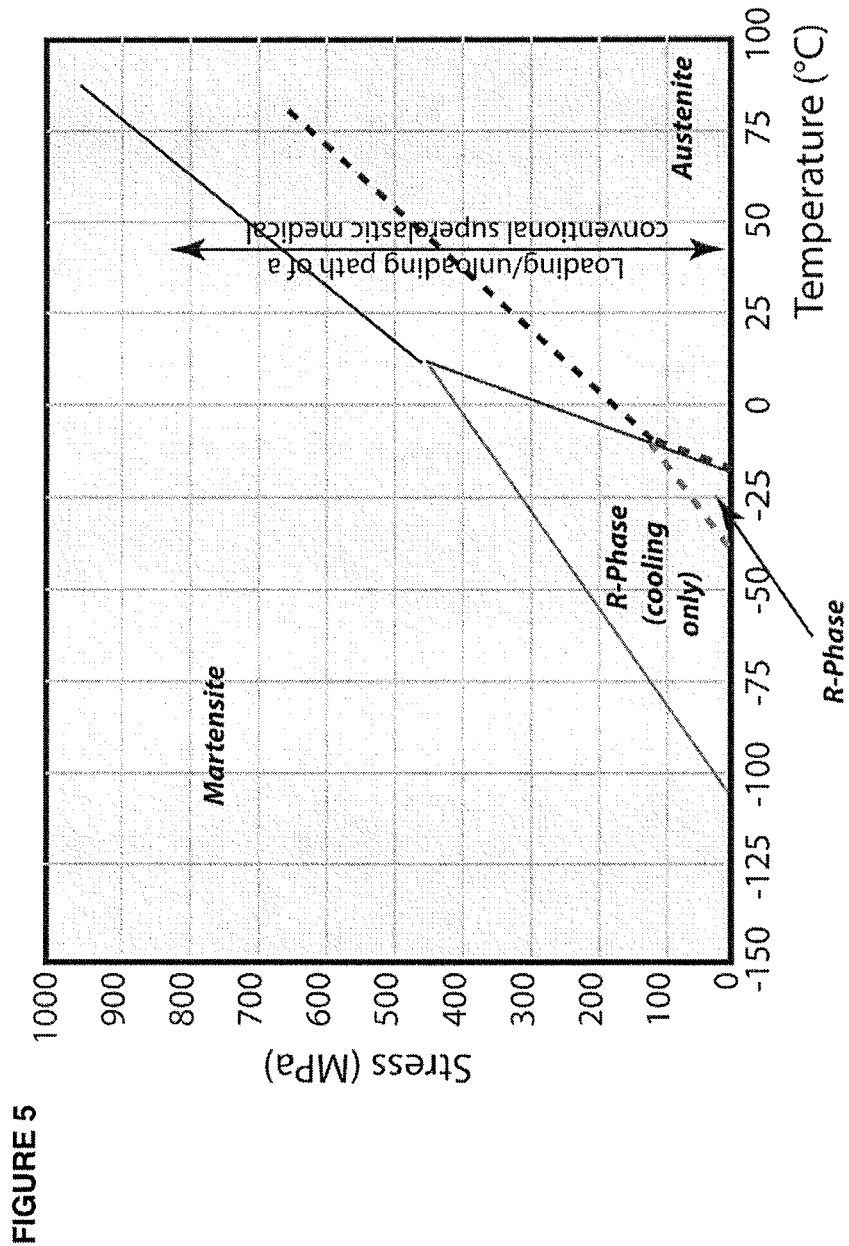
FIG. 5 is the same diagram as shown in FIG. 4, but with a vertical line indicating the loading and unloading path of a conventional superelastic medical device, echoing the behavior of FIG. 1. Note that the loading path goes from Austenite to Martensite, and the unloading from Martensite to Austenite.

FIGS. 4 and 5 simply show an overlay of the FIGS. 3A and 3B (the "forward" and "reverse" directions respectively, defined more fully in the figure caption). Note that the stability domain is much more limited in the reverse direction than the forward direction. FIG. 4 shows the transformation temperatures (measured at zero stress) and FIG. 5 shows the loading and unloading trajectory that takes place in a stress-strain test such as FIG. 1—again, loading resulting in the formation of Martensite from Austenite and unloading, the reversion of the same.

The conventional nitinol design parameters referenced in the background section would stipulate that medical devices should be made with an $A_f$ temperature below body temperature, in order to assure that unloading completely restores the structure to Austenite, and thus restores the original, undeformed shape. Considering normal variation in body temperature, in combination with uncertainty in measuring transition temperatures, the $A_f$ temperature of conventional medical components is typically required to be specified at least 3-5° C. below body temperature, or at most 32-34° C. In materials and devices designed under this former conventional paradigm, the R-phase plays no role in superelasticity.

Differential Scanning calorimetry is often used to measure the stress-free transformation temperatures indicated on FIG. 4. An example of such an experiment is shown in FIG. 6A with key phase transformations indicated. Note that this is not the same alloy as used to create the phase diagram in FIG. 4, but also represents a typical superelastic alloy that might be used in a medical device.

In FIG. 6A, the test begins at point A, where the sample is fully B2 Austenite. Cooling from point A, the sample begins to transform from Austenite to R-phase at B ($R_s$), this transformation reaches a peak at C($R_p$), and transformation to R-phase is complete at point D ($R_f$). The sample is fully R-phase from point D to E. The transformation to B19' Martensite begins at point E ($M_s$), reaches a peak at F ($M_p$), and is complete at point G ($M_f$), completing the forward transformation of the material. Now reversing from cooling to heating, the B19' Martensite begins to revert to R-phase at H ($M^*_s$), and this transformation reaches a peak at I ($M^*_p$). The material next reverts from B19' Martensite to R-phase (M→R), and subsequently the R-phase reverts to B2 Austenite (R→A). The M→R and R→A transformations partially overlap, so the completion of M→R ($M^*_f$) and beginning of R→A ($R^*_s$) can not be easily isolated in this diagram. However, the peak of the transformation from R-phase to B2 Austenite can be seen at L ($R^*_p$). The R→A transformation is complete at M ($R^*_f$), which also corresponds to the Austenite Finish ($A_f$) temperature. Even though the R-phase is intermediate to the reversion of Martensite to Austenite in the stress-free condition of FIG. 6A, the R-phase may still have no role in the superelastic process: unloading Martensite may still revert directly to Austenite without the intervention of the R-phase, even though the R-phase is intermediate during thermal reversion. This, for example, would be the case for an alloy described in FIG. 4.

Figure 6B:
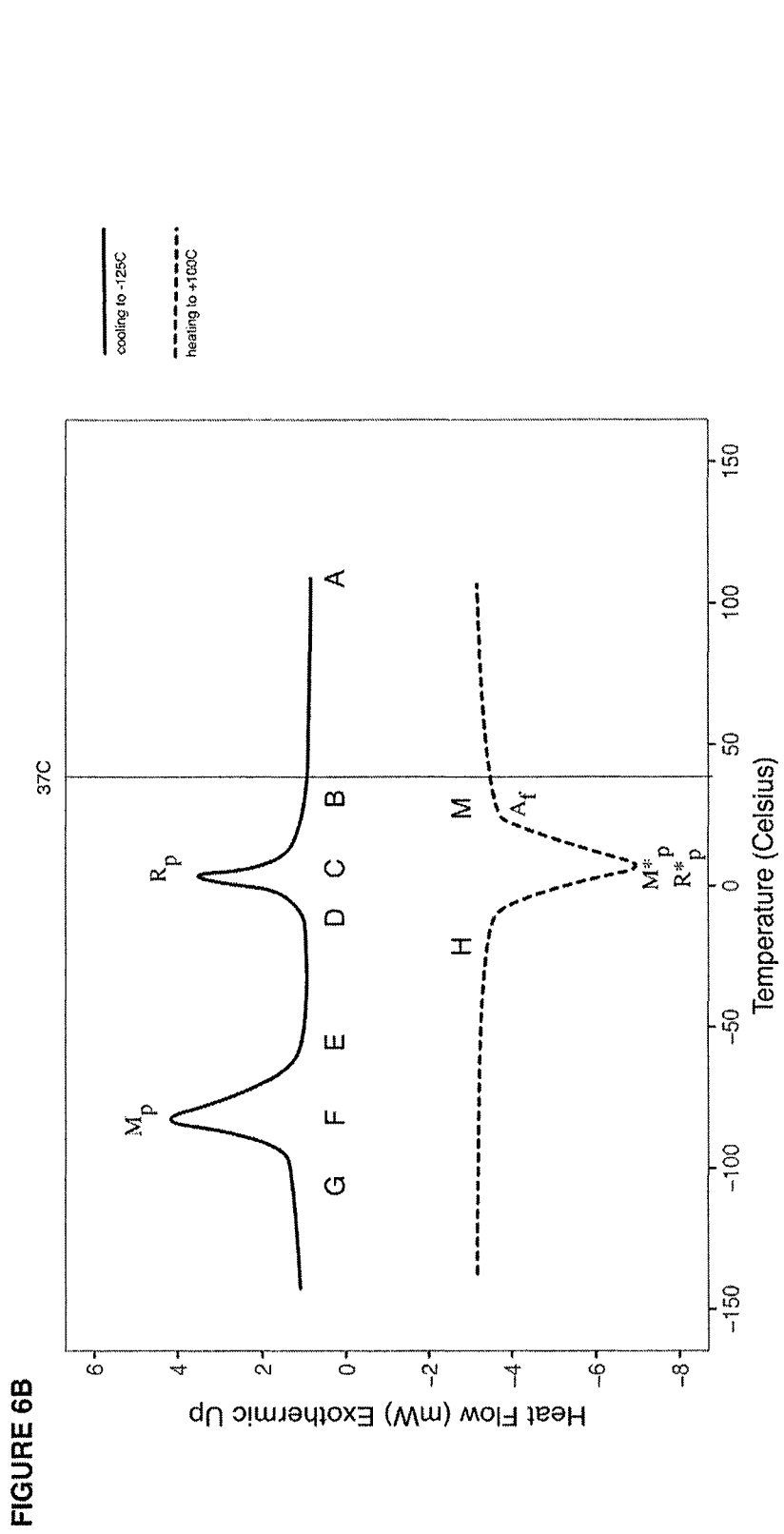
FIG. 6B is a variation of FIG. 6A, wherein the stress-free reversion temperatures of Martensite and R-phase are so close as to be indistinguishable by typical DSC testing.

FIG. 6B illustrates another condition that may be observed in medical components fabricated using processes common in the prior art. In this condition, the reversion from B19' Martensite to R-phase (M→R) and R-phase to Austenite (R→A) occur at temperatures close enough to be indistinguishable using typical DSC testing as shown here.

In one aspect, there are provided methods to make a medical device from an alloy where superelasticity occurs predominantly between R-phase and Martensite rather than between Austenite and Martensite as is common in conventional superelastic medical components. This, for example would occur if $A_f$ is above body temperature, and even better, when $A_p$ is above body temperature, or even more ideally, when $A_s$ is above body temperature.

Figure 7:
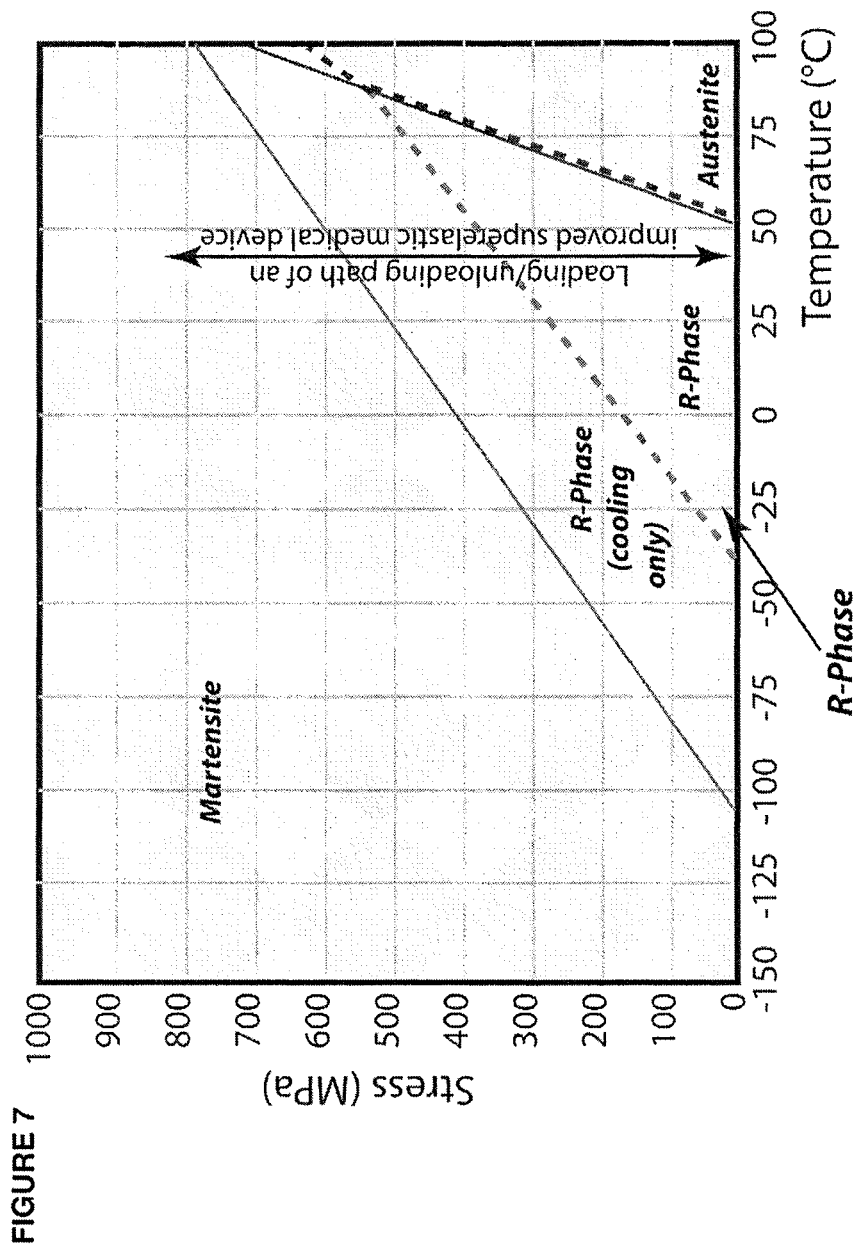
FIG. 7 is the same diagram as shown in FIG. 5, but now for an alloy in which the R-phase has been stabilized so that it is now the stable phase at body temperature. Note that the loading path goes from R-phase to Martensite, and the unloading from Martensite back to R-phase.

The phase diagram for an alloy that would qualify as a superelastic material where superelasticity occurs predominately between R-phase and Martensite is shown in FIG. 7. Here the R-phase has been stabilized with respect to Austenite. Martensite forms and reverts at roughly the same temperatures, but now the trajectory of a loading-unloading curve (such as that shown in FIG. 1) goes from R-phase to Martensite and back. A vertical line is provided on the curve with exemplary R-phase to Martensite loading and unloading occurring at or near body temperature.

EXAMPLE SECTION

Figure 8A:
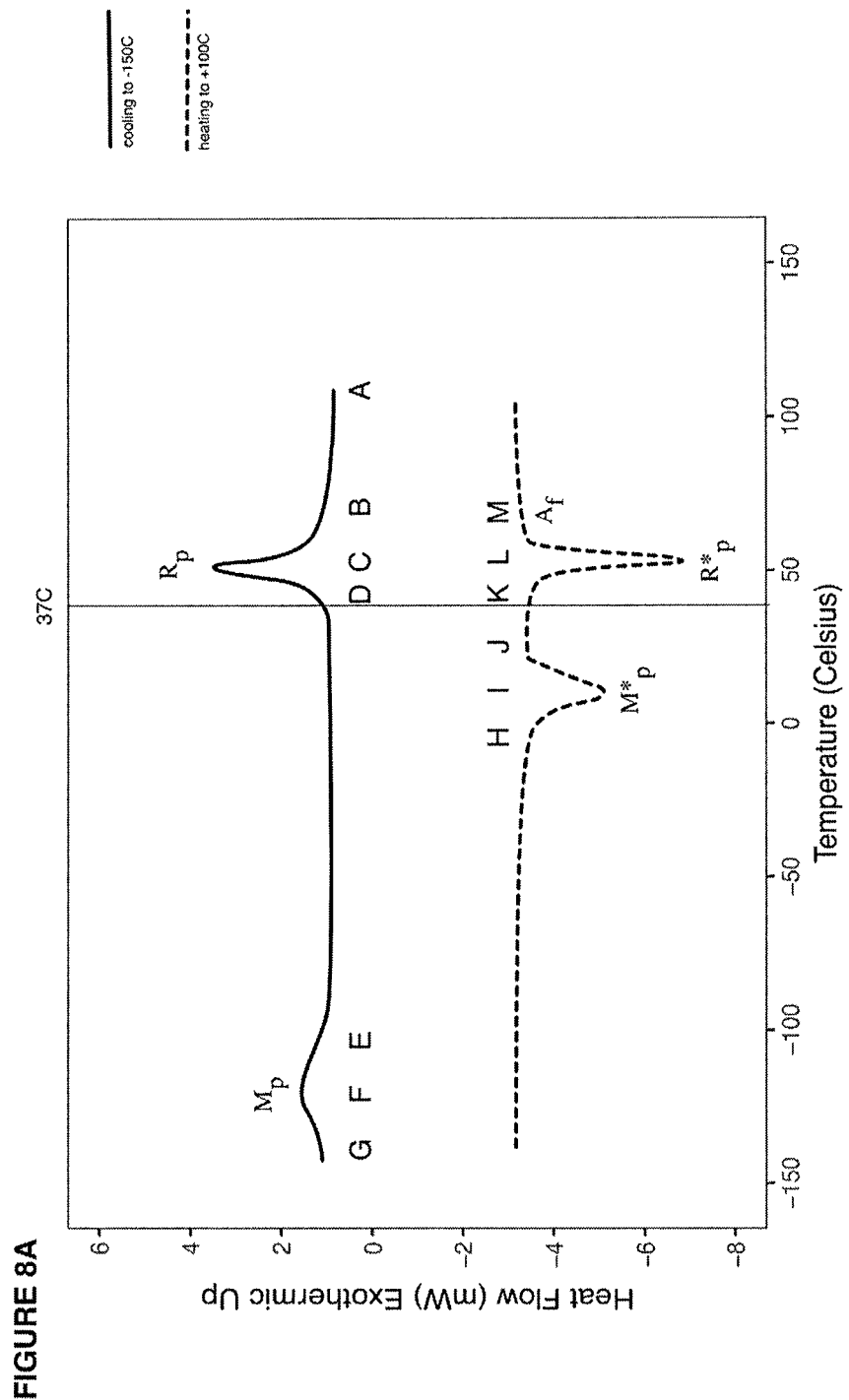
FIG. 8A is a DSC curve for the improved process, where the R-phase has been stabilized and shifted above body temperature, corresponding to FIG. 6.

To demonstrate one specific embodiment of an inventive process, begin with a Titanium alloy wire material having 50.8 wt. % nickel, with a final cold working diameter reduction of 45% area reduction. Age the wire under tensile stress at approximately 550° C. to cause the wire to adopt a straight configuration. Next, further age the wire at 250° C. for 105 hours, thereby stabilizing the R-phase with respect to Austenite. The DSC curve that results from such a treatment is shown in FIG. 8A. In this condition, R-phase has been stabilized and shifted to above body temperature, corresponding to FIG. 7. Turning now to FIG. 8A, the test begins at point A, where the sample is fully B2 Austenite. Cooling from point A, the sample begins to transform from Austenite to R-phase at B, this transformation reaches a peak at C($R_p$), and transformation to R-phase is substantially complete at point D. The sample is fully R-phase from point D to E. The transformation from R-phase to B19' Martensite begins at point E, reaches a peak at F ($M_p$), and is substantially complete at point G, substantially completing the forward transformation of the material. Now reversing from cooling to heating, the B19' Martensite begins to revert to R-phase at H, and this transformation reaches a peak at I ($M^*_p$). In contrast to the response of many conventional materials as depicted in FIG. 6, the reversion from B19' Martensite (M→R) in this illustrative example is distinctly separated from the subsequent reversion of R-phase to Austenite (R→A). Therefore, unlike in FIG. 6, the start and finish of each peak can be observed. The reversion of B19' to R-phase is substantially complete at J ($M^*_f$), and the material remains in the R-phase from point J to K. The transformation of R-phase to B2 Austenite begins at J, peaks at L, and is substantially complete at M, which also corresponds to the Austenite Finish ($A_f$) temperature in this particular example.

As can be seen in FIG. 8A, the stable phase with no stress applied remains in the R-phase well above body temperature (37° C.), advantageously, and in contrast to conventional NiTi superelastic components. Loading will therefore stress induce Martensite from the R-phase and unloading will revert Martensite to R-phase. The resulting stress-strain curve is shown in FIG. 9A.

Figure 9A:
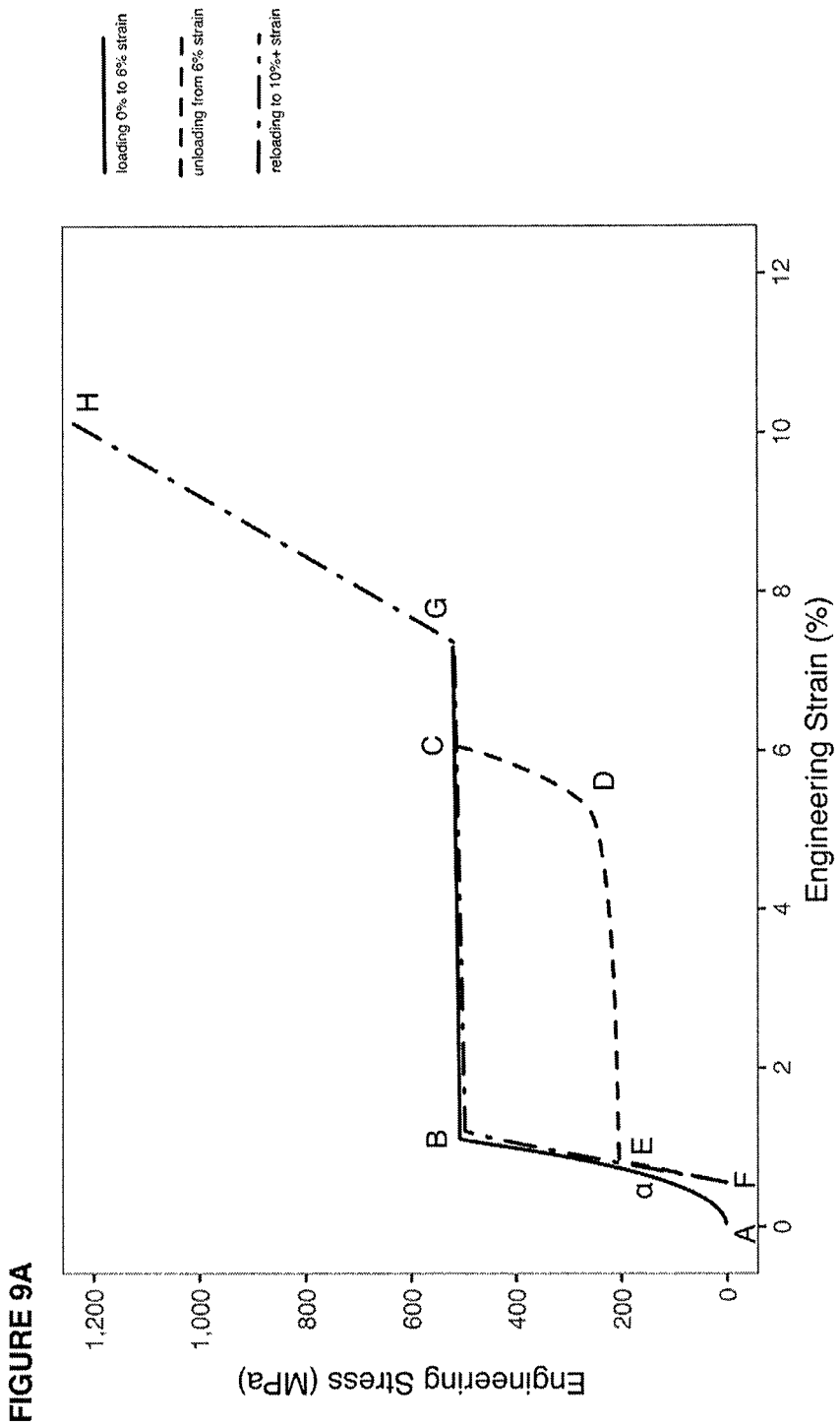
FIG. 9A is a superelastic stress-strain curve of the material shown in FIG. 8A, beginning with the R-phase and finishing with Martensite, then reverting to the R-phase upon unloading.

FIG. 9A is a superelastic stress-strain curve of the material shown in FIG. 8A, tested at a constant temperature of 37° C., beginning with the R-phase and finishing with Martensite, then reverting to the R-phase upon unloading. The qualifications regarding volume fraction of Martensite related to polycrystalline material, discussed in the context of conventional A-M-A superelasticity above (FIG. 1) also apply to the presently discussed R-M-R superelasticity. The specimen is substantially fully R-phase from point A to B. Reorientation of the R-phase is seen from point A to α, and the effective elastic modulus of the R-phase from a to B. The specimen partially transforms from R-phase to B19' Martensite from B to C. Unloading from point C, the transformed B19' material reverts to R-phase from D to E, returning to essentially all R-phase at point E. Continuing to unload from E to F, the specimen follows the R-phase elastic modulus previously observed between α and B. In this condition, the R-phase reorientation is not recovered at zero stress, as shown by the residual deformation indicated by the gap between A and F. From point F, the specimen is re-loaded following the R-phase modulus to point B, now substantially fully transforms from R-phase to B19' Martensite from B to G, and is "fully" martensitic at point G. Loading from G to H, the specimen is loaded in Martensite. Continued loading past the elastic limit of Martensite will result in plastic deformation of the material.

A material produced according to some embodiments of the inventive methods to have the properties as shown in FIGS. 8A and 9A still exhibits superelasticity, but does not fully return its original shape. This is because the R-phase is itself a martensitic phase and is easily able to accommodate approximately 0.5% strain. Whilst Austenite is a single fixed structure, the R-phase offers several variants to which reversion can take place and thus creates the observed residual strain (see the gap between A and F in FIGS. 9A and 9B). This strain accommodation is also described as R-phase reorientation. In still other variations, where one desires to proceed to use an inventive material without any of the aforementioned observed residual strain, the inventive material may undergo heat treatment sufficient to revert the R-phase to Austenite. The result of such additional heating is that the recovery would further itself and become more perfect.

Figure 10A:
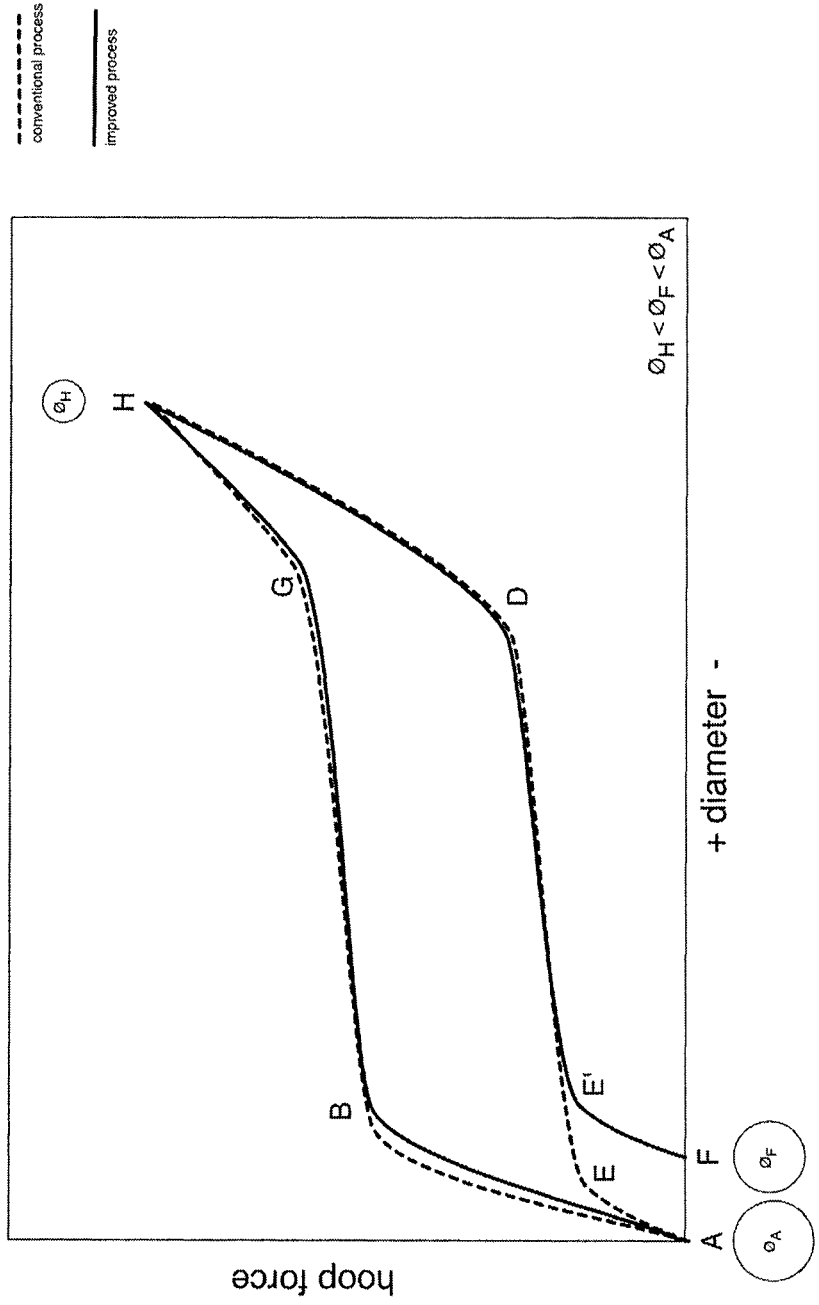
FIG. 10A is the residual set of an R-M-R superelastic device (MRM) schematically shown and correlated to a stent. Diameter $Ø_A$ represents the original manufactured diameter, $\emptyset_F$ the intended or designed diameter to which it must return upon unloading, and $\emptyset_H$ represents the diameter within a catheter.

The 0.5% or so residual strain illustrated in FIGS. 9A and 9B may be anticipated in the design of such a device. In one illustrative use of an embodiment of this invention in a stent, for example, one would create a first undeformed shape that is a larger in diameter than the minimum acceptable diameter after deploying, as illustrated in FIG. 10A. Here, one manufactures a device by shape setting the diameter shown at $Ø_A$ which is then the Austenitic shape. In the material shown in FIG. 9A, deformation, such as the crimping of a stent, produces diameter $Ø_H$ and releasing the constraint at body temperature results in diameter $Ø_F$ which is represents the shape that is accommodated by the R-phase. Diameter $Ø_F$ rather than $Ø_A$ must also be the minimum diameter that is required to function in the vessel. In the prior art, it would be $Ø_A$ that would be the minimum acceptable diameter. Additional hoop force-diameter details are appreciated with reference to FIG. 10B.

With reference to FIG. 10A, it is noted that a subsequent crimp to $Ø_H$ will still return to $Ø_F$. As a result numerous processing and manufacturing options are available. One may add the first crimp to the end of manufacturing cycle and achieve a device that fully recovers its shape without reverting to Austenite. Such a step will remain effective so long as in later processing the device is not subsequently heated above $A_f$.

Figure 8B:
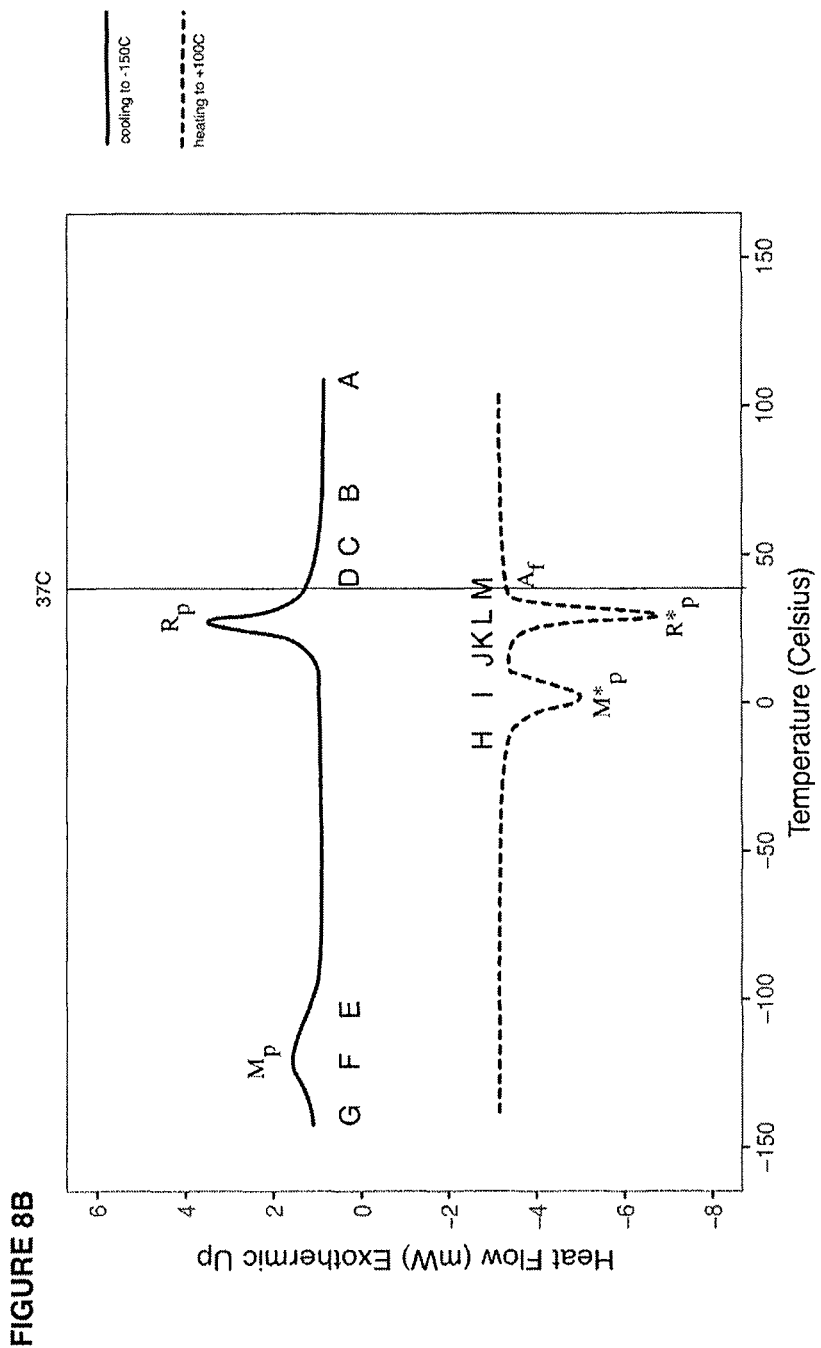
FIG. 8B is a DSC curve for the improved process, where the R-phase has been stabilized and shifted to a temperature at or near body temperature.

While FIGS. 8A and 9A describe exemplary and advantageous embodiments characterized by stress-free R-phase stability at or above body temperature of 37° C., it should also be noted that alternate embodiments are possible which may provide similar advantages and benefits. Two such additional embodiments will be described with reference to FIGS. 8B and 9B. FIG. 8B is a DSC plot for such a variant of the inventive process, with R-phase reversion below body temperature. As shown, R-phase reversion to Austenite is substantially complete at body temperature, indicated by point M. Therefore, in the stress-free state, the $R^*_f$ is approximately equal to body temperature. In this condition, because the $R^*_f$ peak stabilized at a temperature distinctly above $M^*_f$, $R^*_f$ also corresponds to $A_f$. Similarly, the stress-free initial formation of R-phase, indicated by D, is also approximately equal to body temperature. It should be noted that in presence of applied stress, as is typical for medical applications, the material as shown here may stress induce R-phase at 37° C., as shown in FIG. 9B.

FIG. 9B is a variation of FIG. 9A, wherein Austenite is originally stable at 37° C. The stress-strain response initially follows the Austenite modulus from A to λ. Continuing to apply stress, R-phase reorientation is seen between λ and α, and loading continues along the R-phase modulus from α to B. Subsequent characteristics in stress-strain response follow the same path as in 9A, including unloading from E to F along the R-phase modulus, and residual deformation in the stress-free state as seen by the gap between A and F. As with FIG. 9A, FIG. 9B illustrates deformation related to R-phase reorientation may not be recovered in the absence of an elevated temperature or additional applied stress.

Figure 10B:
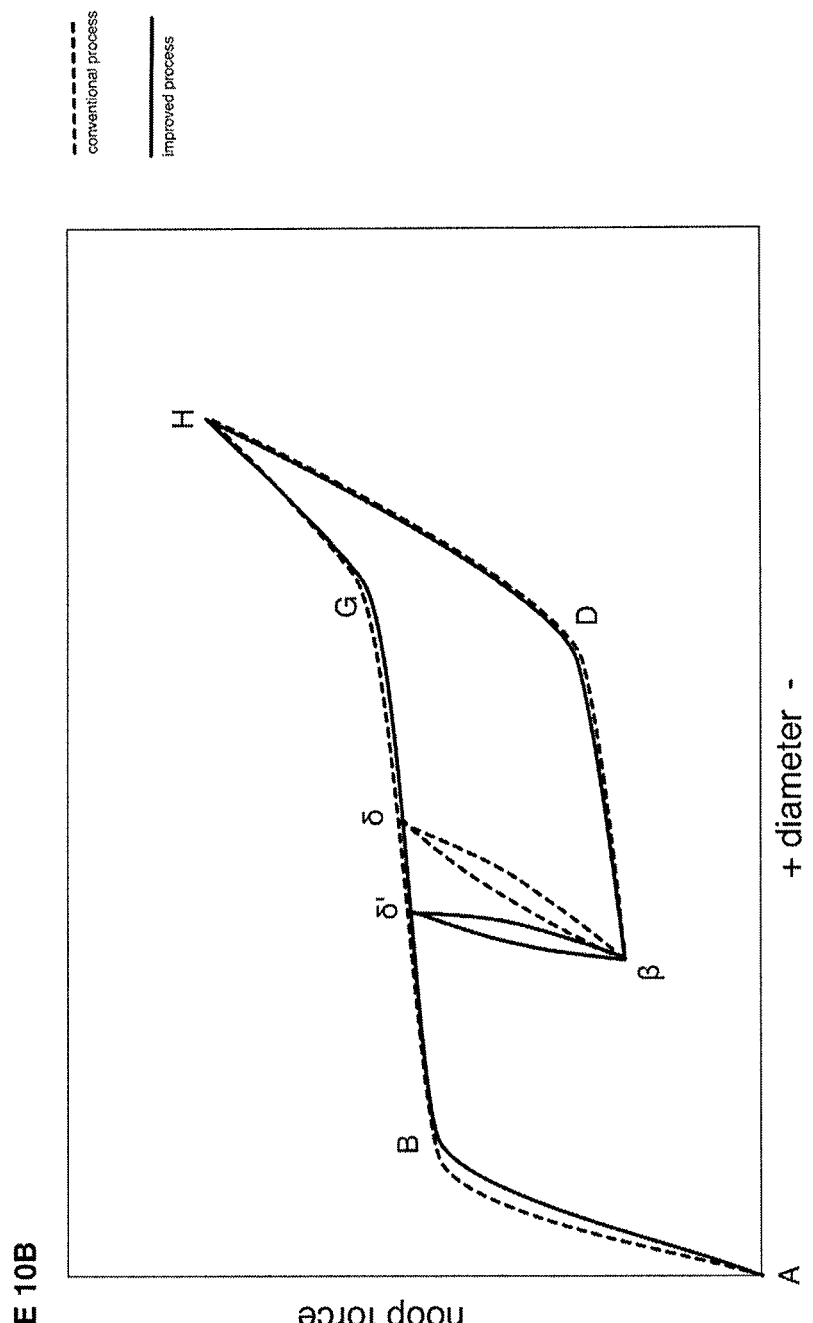
FIG. 10B provides additional hoop force-diameter information with respect to FIG. 10A.

Still additional aspects of the various inventive materials are appreciated with reference to FIGS. 10A and 10B. In FIG. 10B, a stent formed using an inventive process described herein when deployed in an artery, for example, might reach an equilibrium diameter at β then be cyclically loaded along the solid path in to δ'. This cyclic loading is referred to as the "duty cycle." The cyclic loading experienced by a particular medical component will depend upon a number of factors such as, for example, the physiological environment, specific anatomical constraints of a healthy or a diseased implantation site, or other characteristics that exemplify the in-vivo location where the medical component will reside in use. As such, cyclic loading may be due, for example, to the cardiac cycle, breathing, or skeletal-muscular forces. It is highly desirable that the so-called duty cycle strain is not so great as to cause the duty cycle to proceed onto the upper loading plateau—should this happen, that means the volume fraction of Martensite is increasing and decreasing with the duty cycle, causing a hysteresis and microscopic damage to the material. If, however, one loads the device so as to keep the duty cycle at or below point δ', then most or all of the duty cycle can be accommodated elastically, and fatigue damage avoided.

Figure 11A:
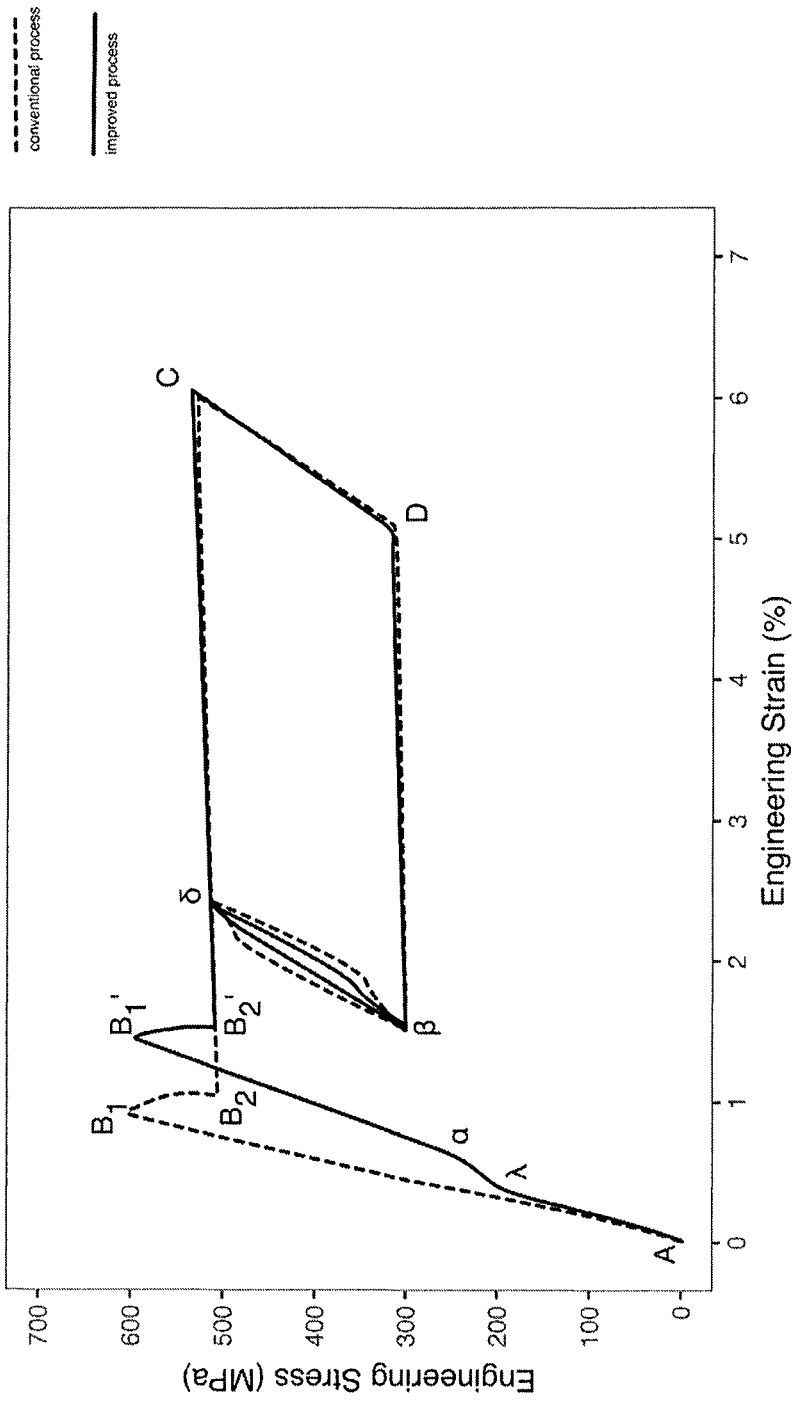
FIG. 11A is a comparison of the cyclic stress strain loops of conventional and new processes. The dashed line shows conventional loading of Austenite and an upper plateau due to the formation of Martensite—then unloading to a plateau of predominantly Martensite/Austenite. After unloading to a 1.7% strain, the device is cyclically loaded between 1.5 and 2.3% strain (see close-up in FIG. 11B). The solid lines shows the same experiment, but now the unloading plateau is predominantly R-phase/Martensite, and the resulting hysteresis is narrower due to the lower stiffness of the R-phase/Martensite mixture.

FIG. 11A illustrates these concepts with actual data from fatigue testing of material specimens processed by conventional vs. improved processes, tested at a constant temperature of 37° C. in uniaxial tension. The dashed line represents the conventional process. Starting at A, the specimen is fully austenite until B1, at which point transformation to Martensite begins with the formation of Lüders bands, which relieve the stress to B2. Transformation of austenite to B19' Martensite continues from B2 to C, and the test is reversed at 6% strain. B19' Martensite partially reverts to B2 Austenite between D and β. The fatigue duty cycle then alternates between points β and δ, with the material alternating between B19' Martensite and B2 Austenite. If unloading were to be completed to zero stress, in this case the device would again be fully austenitic, but in practice, the device is not fully unloaded, rather it comes to a stress equilibrium with its surroundings at point β. At this point β, we have a mixture of A and M, with volume fraction of M increasing as one increases the strain toward point D.

The solid line represents one embodiment of the improved process. Like the conventional process, this specimen begins at A in a fully austenitic state. Unique to this embodiment, at point λ, Austenite is transformed to R-phase in a stress-induced phase transformation. Reorientation of R-phase can be seen between λ and α, after which full transformation to R-phase is complete, and loading proceeds to $B_1'$ following the elastic modulus of R-phase. Similar to the conventional process, Lüders bands form at $B_1'$ followed by transformation of R-phase to B19' Martensite from $B_2'$ to C. Unloading follows the same path as the conventional process, now with B19' Martensite reverting to R-phase from D to β. In the improved process, during the duty cycle, the material alternates between B19' Martensite and R-phase, and for the same duty cycle strain as in the conventional case, here we have measurably reduced hysteresis and consequent microscopic damage.

Figures 12A, 12B:
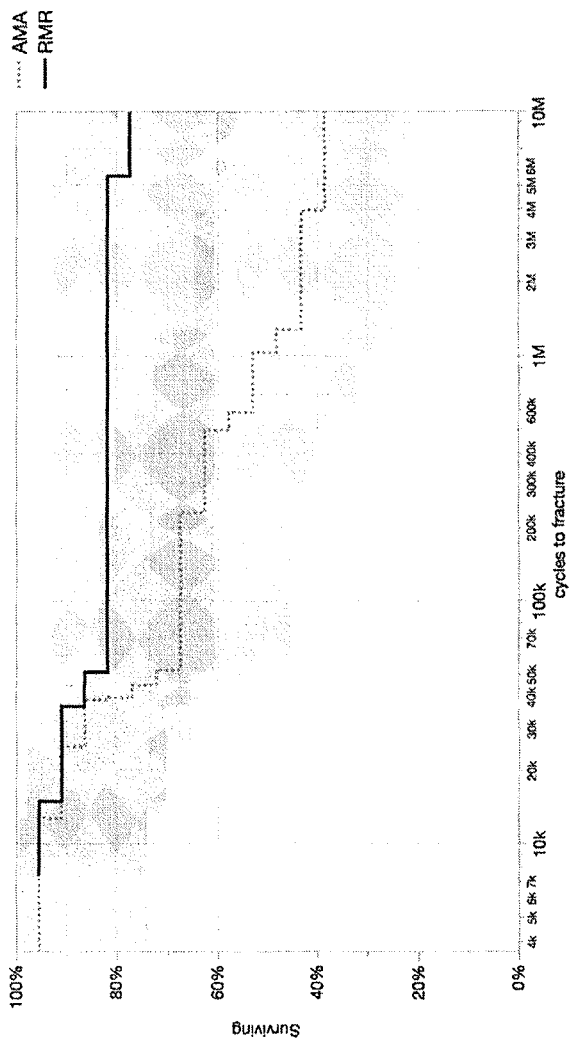
FIG. 12A is a Kaplan Meier survival plot comparing fatigue survival of specimens processed using conventional methods ("AMA"), compared with the inventive process ("RMR"). These experimental results are summarized in the chart of FIG. 12B. The chart in FIG. 12B illustrates the benefits of the inventive process, with a 10 million cycle survival rate of 77% for RMR compared with 41% for a comparable number of AMA specimens with matched strain conditions.

The durability benefits of the improved process are further demonstrated by the experimental results shown in the chart and table for FIGS. 12A and 12B. This figures compare the results of fatigue testing specimens created using the conventional process, labeled AMA (austenite/Martensite/austenite), compared with specimens created using the improved process, labeled RMR (R-phase/Martensite/R-phase). Specimens were fabricated from wire and tested in cyclic tension. Each group includes N=22 specimens, selected from a larger pool of test results to match the population mean strain and strain amplitude as closely as possible in each group, and thereby isolate the effects of the conventional (AMA) vs. improved (RMR) process. Specimens were tested at a constant temperature of 37° C., and testing was stopped when the specimen fractured or upon reaching 10 million cycles. These experimental results demonstrate a significant survival advantage for the improved RMR process (77% survival) relative to the conventional AMA process (41% survival).

Figure 11B:
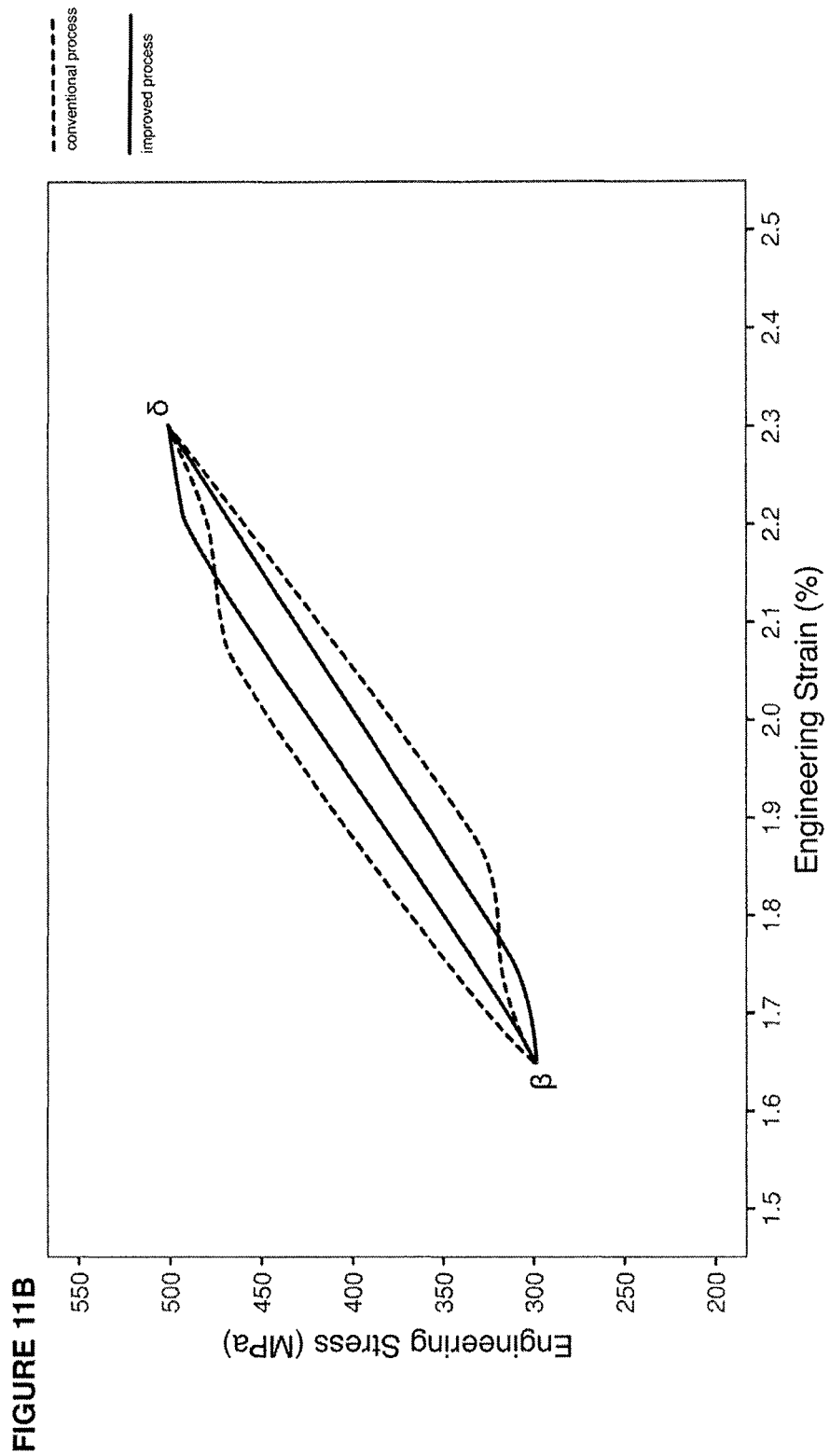
FIG. 11B is a close-up of the duty cycle depicted in FIG. 11A.

According to the previous art ($A_f$ below body temperature), points β and δ of FIGS. 11A and 11B are a mixture of Martensite and Austenite, with the relative amounts of the two phases dependent upon the diameter of point β. According to still another aspect of the present invention, however, point β is mixture of R-phase and Martensite. Since the R-phase has a lower elastic modulus than Austenite, loading will follow a different trajectory: the solid line to point δ. This provides two distinct advantages: (1) the more compliant stress strain response is more physiologically compatible the device is with the surrounding tissue, and (2) the device can be strained to a greater extent without causing fatigue damage and a greater durability will result.

While we have used a stent as an example, the various alternative embodiments of the invention would be of utility in any superelastic device in which either modulus and physical compatibility is important (such as an orthopedic implant) or where durability is important such as in a heart valve, vena cava filter, AAA graft, or other intraluminal medical device or implantable medical device.

To employ some aspects of embodiments of this invention, a medical component or material will be adapted to have the R-phase stable phase at body temperature, yet have the Martensite reversion temperature $M^*_s$ and preferably $M^*_p$ and even more preferably $M^*_f$ be as low as practical, but at least below body temperature. This requires separating the two transformations as much as possible. This separation can be measured in terms of their cooling separation (the $R_p$ and $M_p$ interval), or in terms of heating (separating the $R^*_p$ and $M^*_p$ temperatures). These large separations can be achieved by introducing what can be called microstructural stress fields in the material—such micro stresses bind to the Martensite boundaries and hinder Martensite's ability to grow (suppressing Martensite formation). The most common ways one can create these microstructural stress inhomogenieties by one or a combination of:

(a) Cold work (introducing dislocations and associated stress fields);
(b) Aging (introducing stresses around precipitates);
(c) Adding ternary elements such as Co, Al, or Fe, and, optionally, the addition of other such suitable materials also useful in creating atomic substitutions of atoms with different sizes, and thus local stresses.

Of particular interest in this regard is aging alloys of between 50.5 and 51.5 percent nickel in the 100-300° C. range, an example of which is provided below.

In one embodiment, the inventive material has predominately a mixture of R-phase and Martensite on the unloading plateau rather than Austenite and Martensite. While this is clearly achieved if one begins with the R-phase (under zero stress), we have determined that there is a narrow temperature range in which one might start with Austenite and stress induce the R-phase, still resulting in having predominantly R-phase on the unloading plateau. (see, for example, FIGS. 11A and 11B).

Figure 13A:
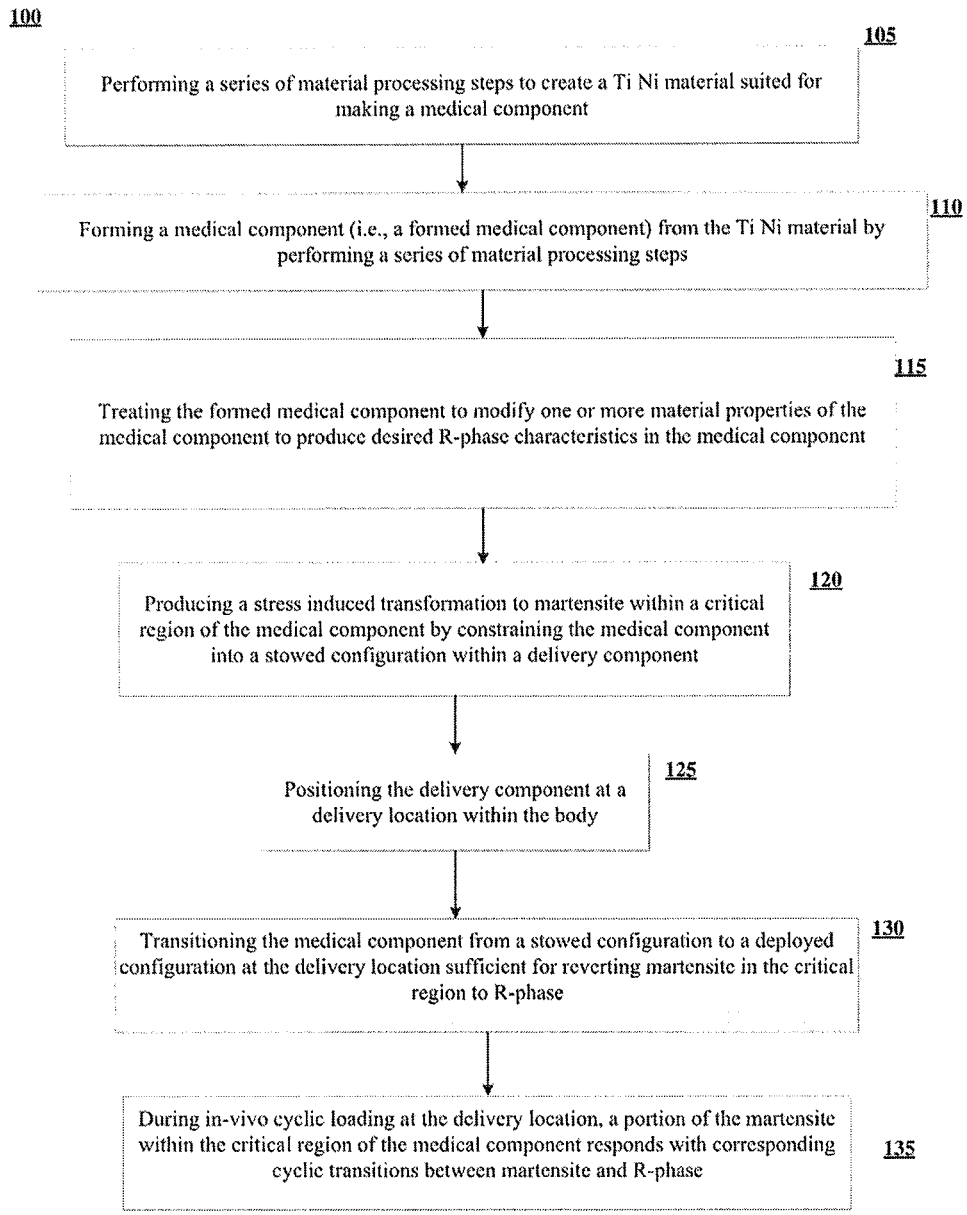
FIG. 13A is an example of a general process flow based on the more detailed process flow diagram described with respect to FIG. 13B.

FIG. 13A is a flow chart of an exemplary method 100 of making and using an embodiment of an inventive medical component as described herein. First, at step 105, there is step of performing a series of material processing steps to create a TiNi material suited for making a medical component. Next, at step 110, there is a step of forming a medical component (i.e., a formed medical component) from the TiNi material by performing a series of material processing steps. Next, at step 115, there is a step of treating the formed medical component to modify one or more material properties of the medical component to produce desired R-phase characteristics in the medical component. Next, at step 120, there is a step of producing a stress induced transformation to Martensite within a critical region of the medical component by constraining the medical component into a stowed configuration within a delivery component. Next, at step 125, there is a step of positioning the delivery component at a delivery location within the body. Next, at step 130, there is a step of transitioning the medical component from a stowed configuration to a deployed configuration at the delivery location sufficient for reverting Martensite in the critical region to R-phase. Finally, at step 135, during in-vivo cyclic loading at the delivery location, a portion of the Martensite within the critical region of the medical component responds with corresponding cyclic transitions between Martensite and R-phase.

Figure 13B:
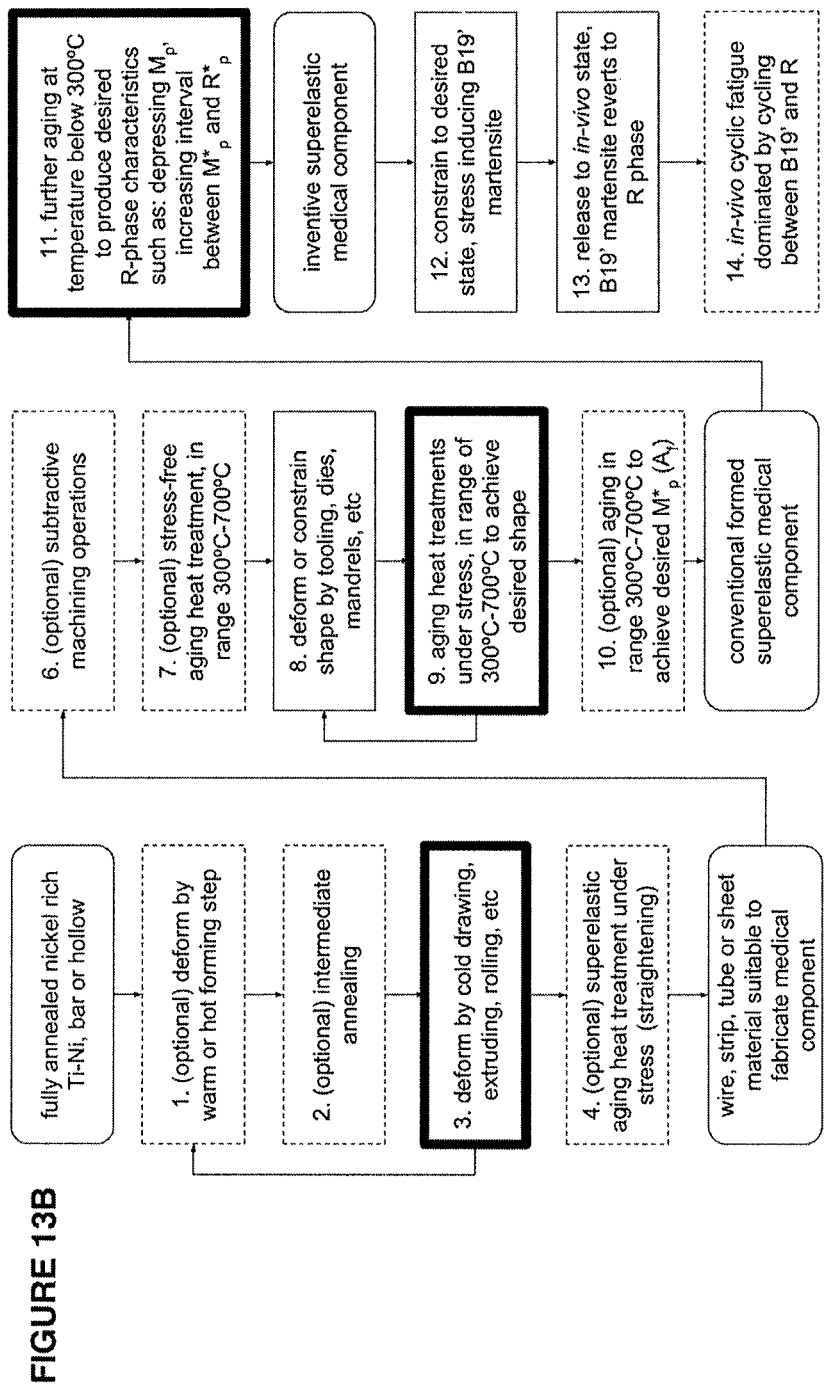
FIG. 13B is a process flow diagram showing steps to produce an example of the present invention. The left column describes the steps to produce materials suitable for fabrication of medical components, the middle column describes steps to fabricate a medical component from such material, and the right column describes the processes to produce the present invention, and its operating characteristics when implanted in the human body.

The above general steps and process flow may be modified in various different embodiments as set forth in FIG. 13B and elsewhere. As is common in the design and fabrication of medical components, certain manufacturing process and methods are favored depending upon the specific medical component being designed as well as the expected operating environment once deployed and in use in-vivo.

In some embodiments, the method 100 is modified to provide a method of processing a TiNi material to produce an implantable medical component by (a) Cold or warm working the TiNi material at least 15%; (b) thereafter, aging the cold or warm worked TiNi material under stress at between 300-700° C.; and (c) thereafter, further aging the TiNi material below 300° C. to produce desired R-phase characteristics. In some additional aspects, a modification of the method includes adaption of the further aging step to be performed under stress or under stress free conditions. In another variation, the step of warm or cold working is 20-50%. In still another variation, the step of aging after the warm or cold working is aging between 500-580° C. In still another variation, the further aging step is between 150-250° C. In still a further variation, the final UTS of the NiTi component is at least 1000 MPa.

In still other various alternatives to the general method 100, there are provided one or more steps for processing a TiNi material to produce a medical component wherein in the medical component has a stress free $M^*_s$ below a normal body temperature. In another variation, there are steps of the method performed wherein the medical component produced has a stress free $M^*_p$ below a normal body temperature. In yet another variation of the method, there are steps of the method performed wherein the medical component produced has a stress free $M^*_f$ below a normal body temperature. In yet another variation of the method, there are steps of the method performed wherein in use in-vivo the medical component produced contains at least some R-phase. In yet another variation of the method, there are steps of the method performed wherein the medical component produced has an R-phase that is stress induced below the lower plateau stress. In yet another variation of the method, there are steps of the method performed wherein a critical region of the medical component produced is substantially R-phase and Martensite. In yet another variation of the method, there are steps of the method performed wherein during a duty cycle applied during in-vivo use the medical component produced alternates between Martensite and R-phase. In yet another variation of the method, there are steps of the method performed wherein the medical component produced has a stress free $A_f$ above body temperature. In yet another variation of the method, there are steps of the method performed wherein the medical component produced has a stress free $A_p$ above body temperature. In yet another variation of the method, there are steps of the method performed the medical component produced has a stress free $A_s$ above body temperature. In yet another variation of the method, there are steps of the method performed wherein temperature separation of the stress free $R^*_p$ and $M^*_p$ is at least 30° C. in the medical component produced by the method. In yet another variation of the method, there are steps of the method performed wherein temperature separation of the stress free $R_p$ and $M_p$ is at least 100° C. in the medical component produced.

Still further, the method 100 may be modified for the production of a variety of different types of medical components from different NiTi materials. In one aspect, the TiNi material is a binary composition comprising substantially only Ti and Ni. In another aspect, the TiNi material has a Ni atomic percentage is 50.5-51.5%. In still another aspect, the TiNi material is a tertiary composition comprising Ti and Ni and at least one other element. In one variation, the at least one other element is a Martensite suppressive material. In still another aspect, the at least one other element is Co, Al, Fe, Cr. In another specific aspect, wherein the at least one element is Co within the range of 0.01 to 3%. In still another specific aspect, wherein the at least one element is Al within the range of 0.01 to 2%. In another specific aspect, wherein the at least one element is Fe within the range of 0.01 to 3%. In still another specific aspect, wherein the at least one element is Cr within the range of 0.1 to 2%. In yet other alternatives, the TiNi material comprises more than 50% atomic volume Ni, from 0.1 to 3% of a Titanium substitution material with remaining composition comprising Ti. In other specific aspects, the Titanium substitution material is one of Hf, Zr, or Nb alone or in any combination.

Against this backdrop, additional aspects of the various alternative inventive methods, materials, and medical components will be appreciated with reference to FIG. 13B.

FIG. 13B summarizes exemplary process steps used variously in aspects of the present invention. Steps 1-10 are common in the prior art, and will be described in brief, noting in particular the influences of process steps that influence the present invention. The combination of steps 3, 9 and 11, highlighted in bold, are to the best of knowledge unique, and from a practical point of view, necessary. Without the cold work (step 3) one lacks the resistance to plasticity needed to make a practical device. Without the first aging under constraint (step 9) one is unable to set the shape accurately. Without step 11, one does not have a sufficiently high $R_p$ temperature to produce a duty cycle that predominantly comprises the R and M phases.

The process begins with fully annealed binary nickel-titanium, preferably with 50.2 to 52.0 atomic % nickel. At this stage, the material is commonly in the form of a solid bar (used to produce wire, strip, or similar forms), or a hollow bar (used to produce tubing). The preferred nickel rich composition is important to later steps which rely upon precipitation of excess nickel. It is understood that the addition of certain elements, such as cobalt, aluminum, or iron can have the effect of suppressing Martensite formation. Therefore alternative embodiments may incorporate such elements, and thereby reduce or eliminate the necessity for precipitation, and therefore reduce or eliminate the necessity for excess nickel.

Solid or hollow bar may be deformed by drawing, extruding, rolling, stamping, or similar processes at optional step 1 to begin transforming the material into a form suitable for medical device fabrication. This step may be performed at temperatures ranging from ambient to 700° C., typically in the range 300° C.-700° C., and preferably between 450° C. and 500° C. In step 2, the material may next optionally be annealed at a temperature of 700° C. or greater. Step 3, essential to the present invention, includes cold forming by drawing, extruding, rolling, or similar methods. This process is typically performed at ambient temperatures, without externally applied heat. Alternatively, any "cold" or "warm" temperatures below the recrystallization temperatures of approximately 600° C. may be used. This step introduces dislocations in the material, and has the effect of increasing the ultimate tensile strength (UTS) of the material. Commonly, the required final form cannot be reached in a single deformation step, and therefore the material is returned to step 1 or 2 for additional forming and/or annealed at a temperature of 700° C. or greater. Steps 1, 2 and/or 3 may be repeated a number of times. For example, reducing bar stock diameter from 10 mm diameter to a 3 mm diameter might require three such cycles.

Still with reference to FIG. 13B, the final material deformation at step 3 commonly includes a desired amount of cold work, at least 15%, preferably 20% to 50% reduction in cross section, and even more preferably 35% to 50%. The network of dislocations created by this cold working step will influence the desirable presence of R phase in a later step. The cold work imparted here also desirably strengthens the material, preferably to an ultimate tensile strength of 1,000 MPa or greater.

Material in the form of wire, tubing, strip, or sheet at the end of step 3 (in an "as-cold-worked" condition) is commonly used as starting material for fabricating medical components. However, in this condition, the material does not have superelastic properties, and typically is not straight. Therefore, many such materials are next subjected to an additional heat treatment, step 4, at a temperature of 300° C.-700° C., preferably between 400° C. and 570° C. This process straightens the material, and imparts desired superelastic properties. Importantly, because this is an aging treatment and not a full anneal, most of the cold work and related dislocation network are retained. The ultimate tensile strength at the end of step 4 is preferably 1,000 MPa or greater. Note that this step is not required—unstraightened wire, tubing or strip can also be subjected to the steps that follow and produce the desired properties.

The steps in the left column of FIG. 13B will influence the properties of the starting material from which the medical component will be fabricated in subsequent steps. The initial composition and unique sequence of deformation steps and thermal treatments will influence characteristics such as grain size, dislocation density, and ultimate strength. These steps also establish the initial stable temperatures for each phase, including initial $M_p$ (B19' Martensite formation) and $M^*_p$ (B19' Martensite reversion) temperatures. $M_p$ and $M^*_p$ control the upper plateau stress (UPS) and lower plateau stress (LPS) respectively, which are important to functional performance characteristics of finished medical components.

The middle column of processes of FIG. 13B, steps 6-10, represent the common practices used to convert starting material into a formed superelastic medical component. Laser cutting, milling, electro-discharge machining (EDM), grinding, or other subtractive manufacturing methods are commonly used to transform the starting material into a desirable geometric form, per optional step 6.

Machining operations as described may impart residual stresses in the material, and may embrittle a layer of material near the cutting surface. Therefore, some processes include an aging heat treatment at step 7. In this optional step, components are aged in a stress free state at a temperature in the range 300° C.-700° C., or preferably between 450° C. and 580° C.

Still with reference to FIG. 13B, steps 8 and 9 are commonly described as shape setting. Analogous to steps 4 (straightening), the objective here is to form the desired shape and then age it to lock that shape in place. The constraint (step 8) may be the application of a stress, or more commonly to fix the shape using physical constraints. This is typically done at room temperature for convenience, but can really be done at any temperature up to and including the aging temperature of step 9. Step 9 actually locks in the shape determined by step 8—for example, aging a stent on a mandrel that is keeping the stent stretched open to a large diameter than it was prior to constraint. The temperature of step 9 can be widely varied, from 350° C. to 700° C., most preferably between 475° C. and 580° C.

Steps 8 and 9 may be repeated as many times as necessary, with specific times, temperatures, and thermal mass, and heat transfer characteristics for each operation influencing the outcomes. Steps 8 and 9 may also be simultaneous in some process variations, wherein the components is deformed (step 8) while at an elevated temperature (step 9). The cumulative effects of these operations will have altered the physical characteristics of the material, such as the phase transition temperatures, and related LPS and UPS properties. Therefore, an optional step 10 is commonly included in the process. In this step, an additional aging treatment is applied to the component, often (but not necessarily) in a stress-free state, to adjust the phase transition temperatures (and related properties) to desirable values. This is often described as "$A_f$ tuning". To be more precise, in the conventional process, aging steps 7, 9, and 10, at temperatures in the range of 300° C. to 700° C., will simultaneously influence all reversion temperatures: $M^*_p$ and $R^*_p$ (and thereby, also, $A_f$). Aging in this temperature range influences precipitation or solution of excess nickel in the form of $Ni_4Ti_3$ precipitates, which have an important influence in the suppression of the B19' Martensite phase, and thermodynamic preference for the R-phase.

The physical, thermal, mechanical, and durability characteristics of the conventional superelastic medical component are fully defined at the bottom of the middle column of FIG. 13B. Stiffness and durability are commonly competing performance requirements: durability is known to be improved with increasing transformation temperatures, while stiffness is simultaneously decreased with increasing transformation temperature. The maximum attainable durability performance is limited by a) the minimum tolerable stiffness, and/or b) the maximum allowable transition temperature. Medical components typically specify a maximum allowable $A_f$ temperature specification of 34° C. or less, to ensure full recovery at body temperature of 37° C.

Within the limits of the current art, the compromise between stiffness and durability cannot be easily avoided, because aging treatments as described above simultaneously adjust all of the phase transition temperatures. Advantageously, the various embodiments of the present invention provide a variety of superelastic materials having individual phase transition temperatures that may be adjusted independently. Accordingly, employing suitable embodiments of the inventive methods, the Martensite formation temperature ($M_p$) can be reduced, thereby increasing upper plateau stress. Additionally, the Martensite reversion temperature $M^*_p$ can be set and held at a reduced temperature, thereby controlling lower plateau stress. As such, improved functional stiffness controls are provided for inventive medical components since the inventive methods herein are attentive to both the upper and the lower plateau stresses together. Furthermore, the R-phase reversion temperature ($R^*_p$) can be separately and simultaneously increased to improve durability performance.

Returning to FIG. 13B, these beneficial improvements are achieved by the further aging treatment described by step 11. Starting, for example, with a conventionally formed superelastic medical component, an aging treatment is applied at a temperature of 300° C. degrees or less, and preferably in the range 150° C. to 250° C. The temperature and time of this aging treatment can be adjusted to achieve a desired suppression of $M_p$ (decreasing the temperature of the forward transformation from R-phase to B19' Martensite), and evolution of $R^*_p$ (increasing the temperature of the reverse transformation from B19' Martensite to R-phase). Unlike conventional aging treatments, the inventive aging treatment at a temperature less than 300° C. has limited influence on $M^*_p$, which controls lower plateau stress and functional unloading stiffness of the component. This further aging treatment often, and even preferably, decreases $M^*_p$. Therefore, the $M^*_p$ temperature can be set to a beneficially low value in steps 9 and/or 10, and maintained during step 11.

When the inventive medical component is used in service, it will typically be deformed, constrained, or compressed prior to insertion in the body. In some cases, a medical component is compressed into a stowed configuration prior to being advanced to a desired in-vivo location. Thereafter, the medical component is transitioned from the stowed configuration to a deployed configuration at the anatomical site where the medical component will function. Such conditions are represented by step 12 in FIG. 13B, during which stress induced B19' Martensite is formed in critically loaded regions of the component. This step of loading a medical device is common to most superelastic medical components, including prior art as well as the present invention.

It is recognized that stress and strain distributions in medical components are often localized to relatively small regions of the geometry, sometimes described as critical regions. In contrast to uniaxial tensile tests as referenced here, local stress, strain, and phase state may vary significantly depending on spatial location and loading conditions. There is often a high gradient of stress and strain near critical regions, and it is at or near such regions that fractures are most commonly observed. Therefore, while the relative volume of critical regions may be quite small relative to the total volume of the medical component, it is in these regions that stress, strain, and phase are most influential.

To illustrate an example of such critical regions, FIGS. 14A-14E represent various parts of a medical component fabricated from nickel rich Ti—Ni wire processed according to the methods of the present invention. The component depicted here could also be fabricated from strip material. In FIG. 14A, the formed component 1401 corresponds to the completion of 115 in FIG. 13A, or 11 of FIG. 13B. Next, in FIG. 14B, the component is subjected to applied loading or deformation in 1402, wherein stress-induced Martensite is formed in critical regions of the component, corresponding to 120 of FIG. 13A, or 12 of FIG. 13B. The applied loading or deformation is partially recovered at body temperature of approximately 37° C. in 1403 (See FIG. 14C), and at least some of the stress-induced Martensite reverts to R-phase in critical regions of the component, corresponding to 130 of FIG. 13A, or 13 of FIG. 13B. In FIG. 14D the component is reloaded in 1404, again converting at least some of the R-phase back to Martensite. The fatigue duty cycle alternates between configurations 1403 and 1404 (FIGS. 14C-14D), corresponding to 135 of FIG. 13A, or 14 of FIG. 13B. A portion of the geometry 1405 in FIG. 14D is magnified in section 1406 of FIG. 14E. The dark area 1408 represents a volume of material that experiences elevated tensile stress and strain, as well as elevated strain amplitude during the duty cycle, relative to the surrounding material 1407. Critical regions such as this, which may be repeated throughout structure, are particularly susceptible to initiation and propagation of fatigue damage. Therefore, it is in critical regions such as these that the benefits of the present invention are most influential.

Figure 15A:
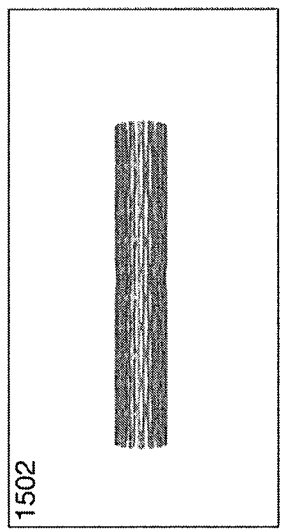
FIGS. 15A-15F illustrate different aspects of several critical regions in an example component formed from tubing or sheet.
Figure 15C:
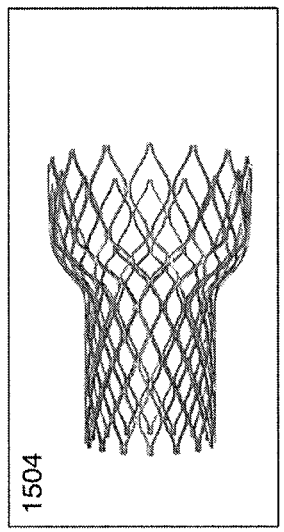
Figure 15B:
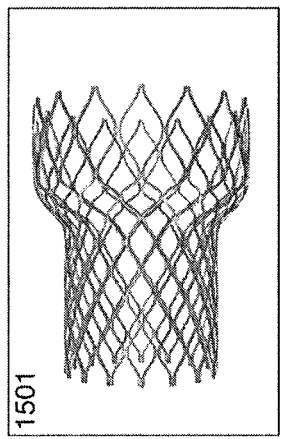
Figure 15D:
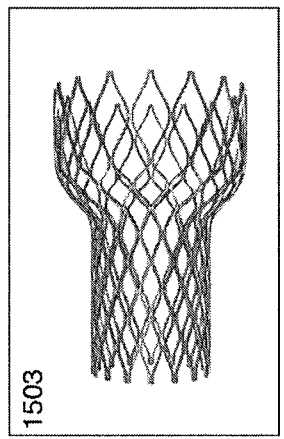
Figure 15E:
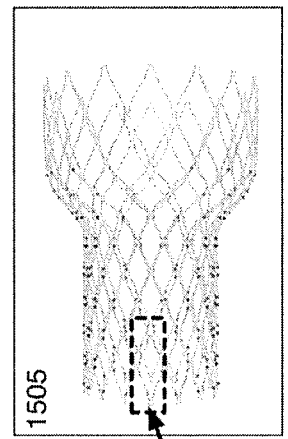
Figure 15F:
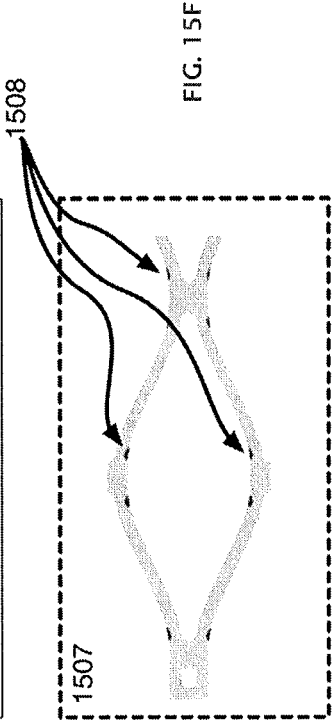
Figure 16A:
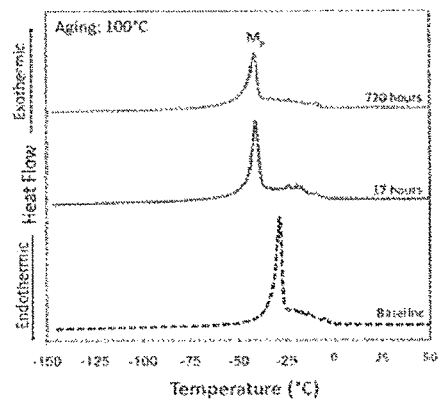
FIGS. 16A-16F illustrate various DSC traces showing suppression of Martensite after aging at 100° C.
Figure 16D:
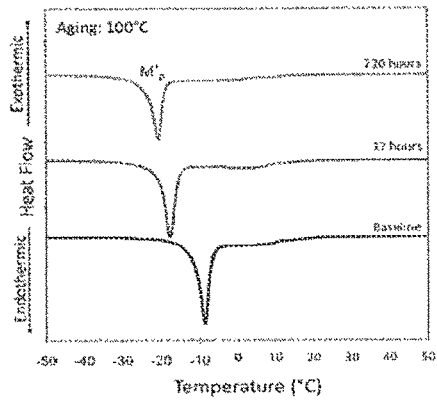
Figure 16B:
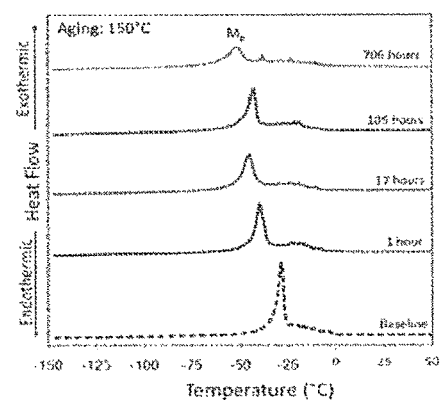
Figure 16E:
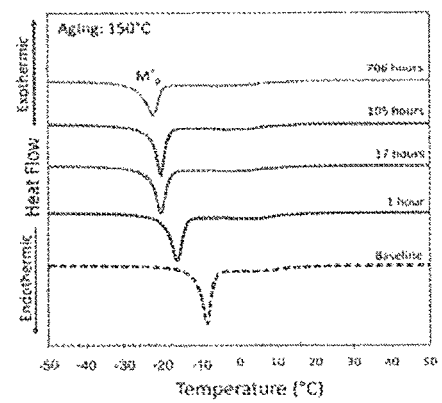
Figure 16C:
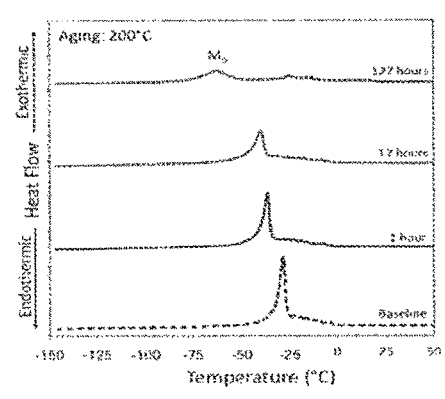
Figure 16F:
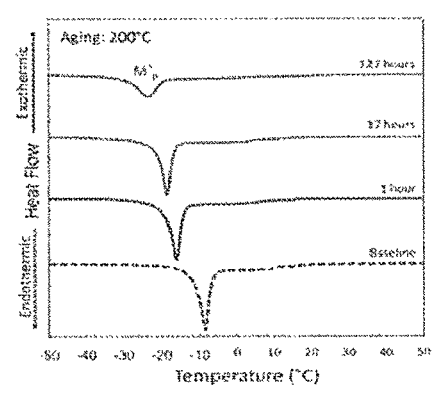

FIGS. 15A-15F represent parts of a medical component fabricated from nickel rich Ti—Ni tubing processed according to the methods of the present invention. The component depicted here could also be fabricated from sheet material. The formed component 1501 in FIG. 15A corresponds to the completion of 115 in FIG. 13A, or 11 of FIG. 13B. The component is constrained to a reduced size in 1502 (FIG. 15B), stress-inducing Martensite in critical regions of the component, corresponding to 120 of FIG. 13A, or 12 of FIG. 13B. Next, in FIG. 15C, diameter constraints are released and the component is partially recovered at body temperature of approximately 37° C. in 1503, and at least some of the stress-induced Martensite reverts to R-phase in the critical regions of the component, corresponding to 130 of FIG. 13A, or 13 of FIG. 13B. FIG. 15D illustrates the component is partially reloaded in 1504, converting at least some of the R-phase back to Martensite if the duty cycle exceeds the material's ability to elastically accommodate the demands of the duty cycle. The fatigue duty cycle alternates between configurations 1503 and 1504 (FIGS. 15C and 15D), corresponding to 135 of FIG. 13A, or 14 of FIG. 13B. Dark regions within 1505 represent volumes of material that experience elevated strain amplitude relative to the surrounding material. In a complex structure such as this, such critical regions often repeat throughout the geometry, most often near hinge point or similar geometrical features. A portion of the geometry 1506 shown in a dotted box in FIG. 15E is magnified in 1507 of FIG. 15F. In FIG. 15F, the exemplary critical regions 1508 are more clearly visible in this view. These regions are susceptible to initiation and propagation of fatigue damage. Therefore, it is in such regions that the benefits of the present invention are most influential. The number, location, distribution, and magnitude of critical regions will vary according to the component design, and loading conditions experienced by the component. While the exact positions and sizes of these regions can be difficult to predict or control, the benefits of the present invention apply uniformly to the entire component, so it is not necessary to know such specific details a priori.

Returning to FIG. 13B, several operationally unique characteristics of an embodiment of the present invention appear in step 13. In step 13, the constraints on the component are released (e.g. it is deployed from a catheter or cannula), and critically loaded regions of the component recover from B19' Martensite to R-Phase as the device recovers to its expanded configuration. We believe that this material response is quite unusual, as conventional medical components are designed to recover from B19' Martensite to B2 Austenite phase at body temperature.

In contrast with conventional superelastic medical components that are designed to avoid R-phase at body temperature, embodiments of the present invention have no such limitation. In fact, in one specific embodiment, the $R^*_p$ (and thereby $A_f$, as in this condition, the $R^*_p$ peak is stabilized distinctly at a higher temperature than $M^*_p$) temperature is set in step 11 to be above body temperature. (See FIG. 13B). Furthermore, in another embodiment, the $R^*_s$ temperature may be set above body temperature, thereby ensuring that R-phase to B2 Austenite transition does not substantially begin at body temperature. As such, the present superelastic medical component may operate in the human body primarily in the R-phase, without any substantial participation of B2 Austenite in critical regions, which is a unique advancement in the field of superelastic materials.

Step 14 in FIG. 13B represents fatigue loading of the medical component resulting from cyclic in-vivo forces and deformations, which may be related to cardiovascular, respiratory, or gait cycles, or other sources of repetitive motion in the body. Unlike conventional superelastic medical components wherein critical regions cycle between B19' Martensite and B2 Austenite, critical regions of the present invention cycle between B19' Martensite and R-phase. The modulus of elasticity of R-phase is less than that of B2 Austenite, so therefore the cyclic modulus of the B19'-R cycle is less than that of the B19'-B2 cycle. Therefore, in the present invention, with a lower cyclic modulus, critical regions can traverse the fatigue cycle with less energy, and thereby accumulate less damage and improved fatigue durability.

It should be noted that the benefits of the present invention may not be completely without costs. Importantly, the component recovers in-vivo to the R-phase configuration, and not to the original B2 Austenite configuration. As the R-phase can accommodate approximately 0.2 to 1% strain, a stent, for example, that has been crimped into a catheter then released from that catheter into the human body will recover in step 13 to a shape somewhat smaller than originally set at step 9 and/or 10. While it would be possible to fully recover the original shape by elevating the deployed component temperature above $R^*_f$ ($A_f$), this might not be possible or desirable if this temperature is above 37° C. Therefore, in the present invention, the designer may choose to compensate for this known shape offset by adjusting the final shape as set in step 8. For example, a cylindrical stent may be formed to a larger diameter to compensate for the known difference between R-phase shape recovery and full recovery to the B2 Austenite shape.

Additional experiments were conducted exploring numerous aspects of the various inventive embodiments including the effect of low temperature aging and the evolution of R-phase in Ni-rich TiNi.

Aging in conjunction with cold work is widely practiced by the medical device industry to shape set, strengthen and adjust the transformation temperatures of Ni-rich Ti—Ni alloys. These three objectives (accurately achieving the desired shape, preventing plastic deformation, and optimizing transformation temperatures) are often at odds: accurate shape setting is promoted by longer times at higher temperatures, maximizing strength requires retaining cold work and thus low temperatures and short times, and controlling transformation temperatures demands the accurate control of the heat treatment temperatures to control the volume fraction of $Ni_4Ti_3$ precipitation and the Ni/Ti ratio of the NiTi matrix. Commonly employed aging/shape setting temperature regimes range from 350° C. to 575° C. Until recently, aging temperatures below 200° C. had been considered too low for precipitation to occur. (See, e.g., J. I. Kim and S. Miyazaki, *Acta Mater.* 53, 4545 (2005). Recent studies, however, have shown that nickel begins to cluster at very low temperatures, eventually yielding to the coherent precipitation of $Ni_4Ti_3$.

The intent of this study is to further explore the low temperature aging of Ni-rich Ni—Ti alloys and its effect on transformation temperatures and mechanical properties. This will be done both in a fully solutionized and annealed condition in which all the excess and free nickel is harbored on the NiTi lattice, as well as in a typical cold worked and aged condition in which some of the nickel has already been precipitated and thus the driving force for further precipitation reduced.

These studies are of interest both to better understand the stability of shape set and aged devices, as well as to explore whether this unexplored aging regime offers interesting properties that are not achievable with the more conventional aging regimes. To the latter point, it will be shown that these regimes allow one to independently control the stability of the two competing martensitic phases: the B19' monoclinic Martensite which we will refer to as "M," as well as the martensitic R-phase, which we will refer to as "R." Moreover, we will also see that low temperature aging offers one some control over the hysteresis of M formation and reversion. Before embarking, a comment on terminology is in order. The shape memory community often uses the Austenite finish temperature ($A_f$) as an indicator of Martensite stability and thus the plateau stresses. The fallacy of this is that it is Martensite reversion that controls the lower plateau, and Martensite seldom reverts to directly to Austenite but rather to the R-phase making $A_f$ moot. Herein we will see some rather exaggerated cases where $A_f$ is highly misleading, including some conditions in which superelasticity is observed well above the $A_f$ temperature. In order to avoid this confusion, we will adopt here a more explicit terminology that identifies the formation and reversion of M and R regardless of the parent phase. A subscripted s, p, or f indicates the start, peak and finish of formation of the indicated phase (e.g., $M_p$ indicates the temperature at which Martensite formation is most rapid), and we will superscript an asterisk to indicate the reversion of the indicated phase, e.g., $M^*_s$ indicates the start of Martensite reversion and $R^*_f$ the completion of the reversion of the R-phase. Therein we will focus on correlating the stresses to Martensite formation and reversion temperatures and not the Austenite finish temperature ($A_f$). The reader can interpolate the other key temperatures from the examples that follow.

First, solutionized samples were cut from a 0.45 mm wide and 160 μm thick straightened strip with 50.8 atomic percent Nickel. Next, an annealing treatment was performed at 750° C. for 5 minutes in a furnace purged with argon and water quenched. Aging treatments were performed as high as 200° C. and as low as 100° C. for durations of 1 hour to one month (720 hours).

The material used for cold-worked samples was a superelastic wire with 0.28 mm diameter oxide-free surface from a 50.8 atomic percent alloy that was cold drawn about 40%, then aged at 530° C. for 4 minutes to fully straighten the wire.

Differential Scanning calorimetry (DSC) were performed on a TA Instruments model Q100 as prescribed by the ASTM F2005 standard for Nitinol (See, https://www.astm.org/Standards/F2005.htm). Tensile tests were performed on an Instron model 5969 equipped with an AVE2 video extensometer and in accordance with ASTM 2516 (See, https://www.astm.org/Standards/F2516.htm) with a displacement rate of 0.5 mm/min. TEM images were taken using an FEI Talos TEM (FEG, 200 kV).

The Solution Treated Condition

FIGS. 16A-16F show, variously, the forward and reverse transformation temperatures after aging fully solutionized material at 100° C., 150° C., and 200° C. respectively. The dashed line at the bottom of each plot represents the unaged baseline condition. The peak transformations are labeled as the formation of Martensite ($M_p$) and the reversion of Martensite ($M^*_p$). In this fully solutionized case, the parent phase in both directions is Austenite—no R-phase is evident.

Figure 17B:
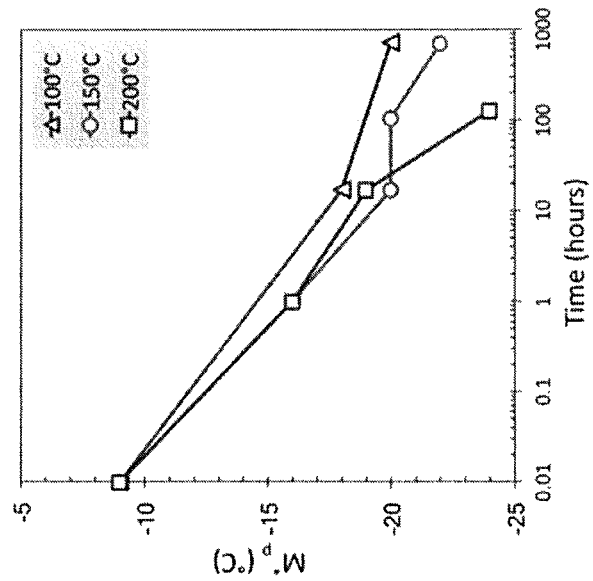
FIGS. 17A and 17B illustrate changes in Martensite formation peak ($M_p$) with exposure time at various aging temperatures (FIG. 17A) and the suppression of Martensite reversion peak ($M^*_p$) with exposure time at various aging temperatures (FIG. 17B).
Figure 17A:
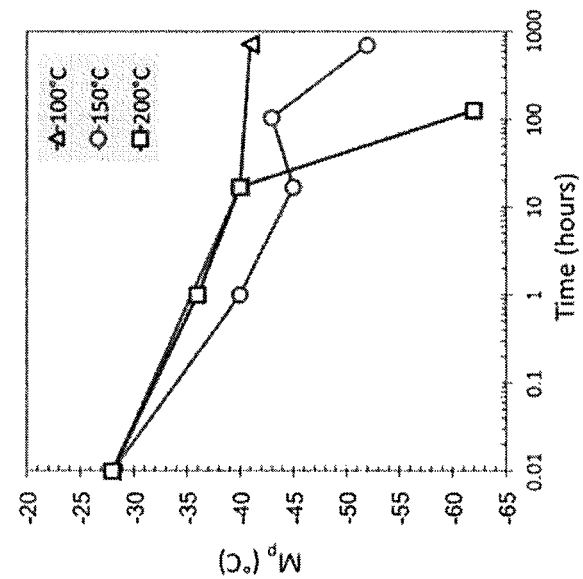

FIGS. 17A and 17B summarize the data, highlighting the suppression of Martensite in both forward and reverse directions. Suppression of the reverse transformation is also more marked than the forward, indicating an increase in hysteresis.

As discussed earlier, aging depletes the NiTi compound of nickel stabilizing the martensitic phase. Yet here we see exactly the opposite effect, the depression of transformation temperatures to and from Martensite a stabilization of the parent phase. But in addition to these compositional or chemical influences, coherent precipitation stresses the lattice and does so in an inhomogeneous manner. Martensite has the ability to better accommodate these stress inhomogenieties and thus is locally stabilized in their vicinity. At the same time, there is an energetic binding between the precipitate stress field and the Martensite, making it more difficult for the Martensite interface to advance. So the coherency stresses have two effects: to elastically distort the B2 lattice itself, and to create pinning centers. And evidently, during low temperature aging, these effects overwhelm the compositional effects. Moreover, the pinning appears to be somewhat more effective in preventing the retreat of the parent phase-Martensite interface than the advance of the interface.

Figure 18B:
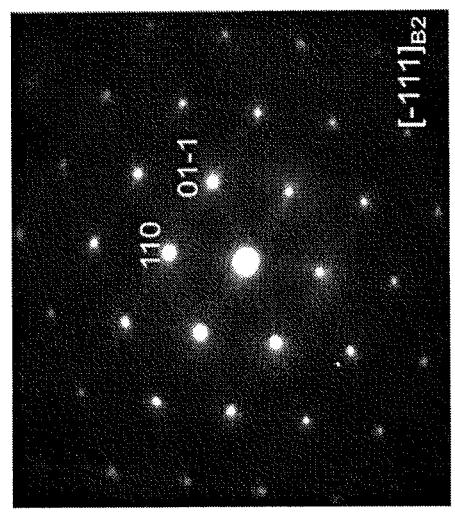
FIGS. 18A and 18B illustrate a high resolution TEM image (FIG. 18A) and associated diffraction pattern (FIG. 18B) of unaged sample (750° C. for 5 min.) showing the presence of B2 structure with no evidence of precipitation.
Figure 18A:
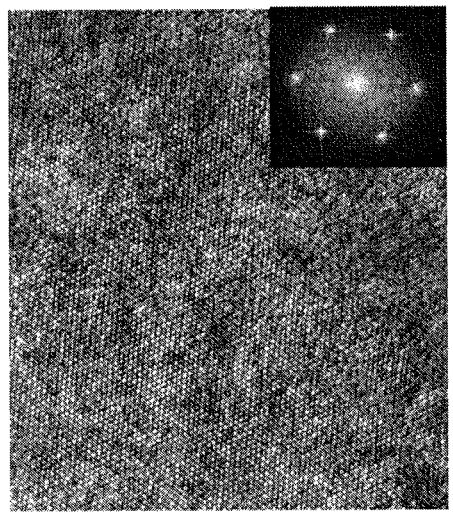
Figure 19B:
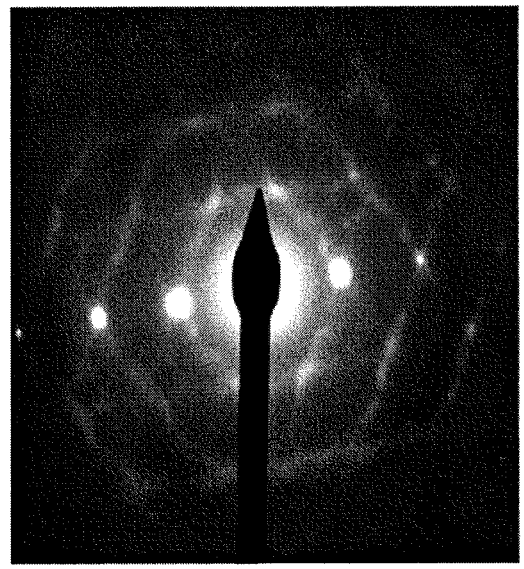
FIGS. 19A and 19B illustrate a high resolution TEM image (FIG. 19A) and associated diffraction pattern (FIG. 19B) of sample aged at 100° C. for 105 hours showing evidence of precipitation. The diffraction pattern also shows diffused intensities along [110] direction evident of Ni clustering.
Figure 19A:
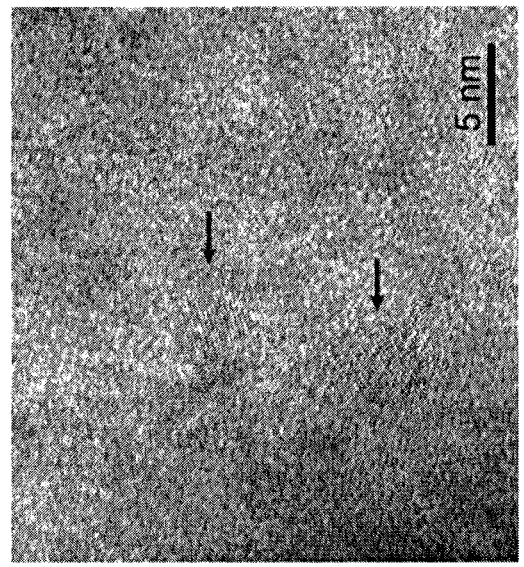
Figure 20A:
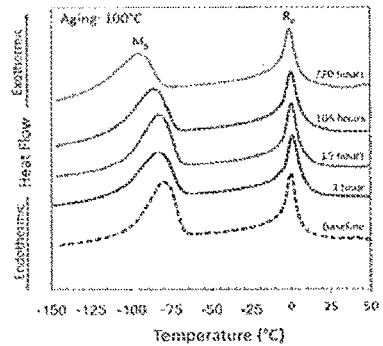
FIGS. 20A-20H illustrate DSC graphs showing forward (FIGS. 20A, 20B, 20C, 20D) and reverse (FIGS. 20E, 20F, 20G, 20H) transformations after aging at 100° C.
Figure 20B:
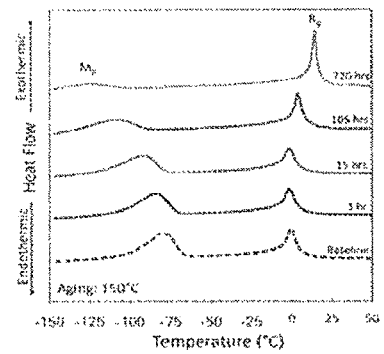
Figure 20C:
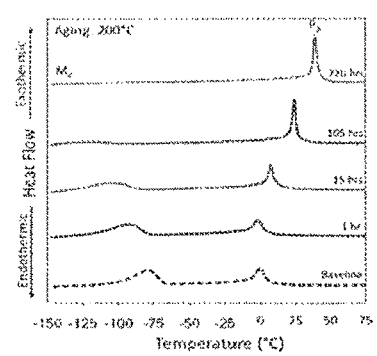
Figure 20D:
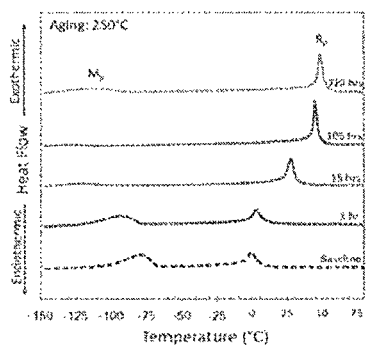
Figure 20E:
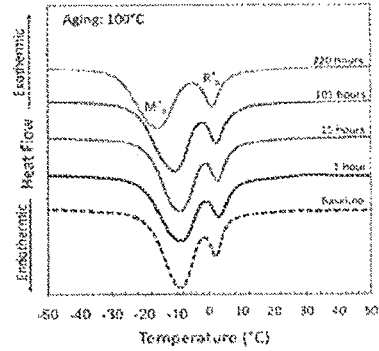
Figure 20F:
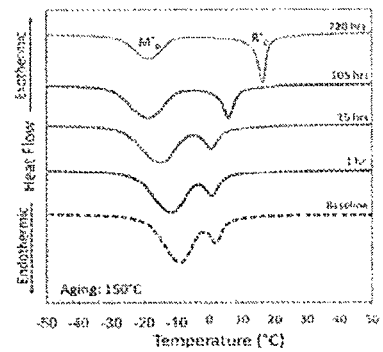
Figure 20G:
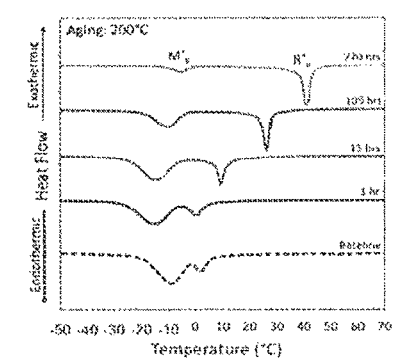
Figure 20H:
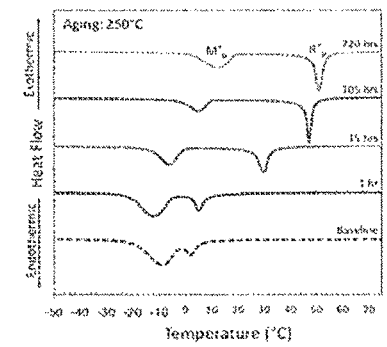

Transmission Electron Microscopy (TEM) was performed to compare the microstructure of the unaged condition (FIGS. 18A and 18B) with strip that was aged at 100° C. for 105 hours (FIGS. 19A and 19B). Both the Selected Area Diffraction (SAD) pattern and the High Resolution TEM (HRTEM) image of the solutionized condition confirm the B2 structure of the Austenitic phase with no evidence of precipitation. In contrast, the aged sample revealed the presence of $Ni_4Ti_3$ precipitates on the order of 5 nm. Also, the SAD pattern showed diffused intensities when sample was tilted along the [110] direction, suggesting evidence of nickel clustering. This observation is consistent with what other researchers have reported. The existence of microdomains in the form of clusters of pure Ni atoms along $<111>_{B2}$ directions is believed to be a precursor to actual precipitation (see S. Pourbabak et al., *Functional Materials Letters*, 10, No. 1 (2017) 1740005). Zheng et al. ascribed the suppression of the B2 to B19' Martensitic transformation to such atomic rearrangement (see Y. Zheng et al., *Acta Mater.* 56, 736 (2008)).

The retained cold-work and aged condition:

FIGS. 20A-20H show variously the forward and reverse transformation temperatures of cold work and aged samples after further aging at 100° C., 150° C., 200° C. and 250° C. The most notable difference between these curves and the solutionized DSC traces is the presence of the R-phase in both the forward and reverse transformation directions. Put another way, the R-phase has replaced Austenite as the parent phase of Martensite, clarifying why it is misleading to use the term $A_f$ when one is interested in the thermodynamics of Martensite reversion. Again, clear aging effects are observed at temperatures as low as 100° C. This is somewhat surprising since the starting condition has already been aged at 530° C. (the "baseline" condition). So while some $Ni_4Ti_3$ is present prior to the additional low temperature aging, there remains a driving force for additional precipitation.

Figure 21B:
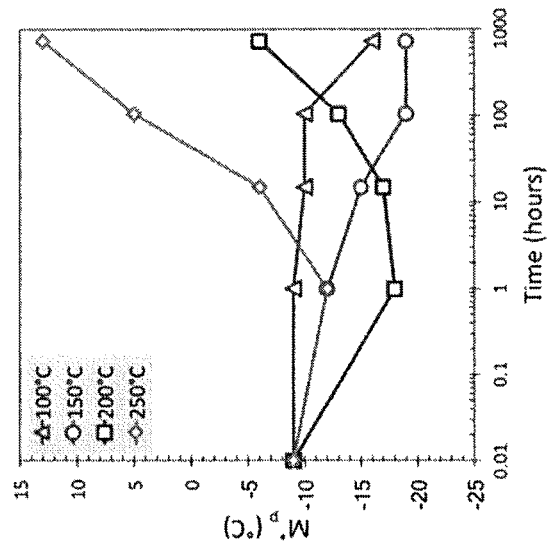
FIGS. 21A and 21B illustrate evolution of the Martensite formation and reversion peaks ($M_p$ and $M^*_p$) with exposure time at various aging temperatures.
Figure 21A:
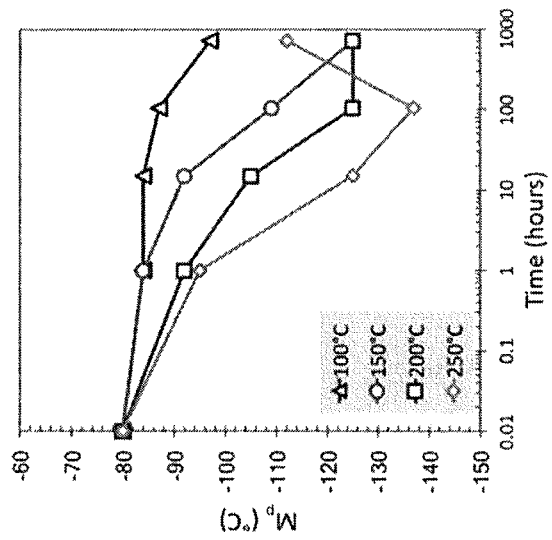
Figures 22A, 22B:
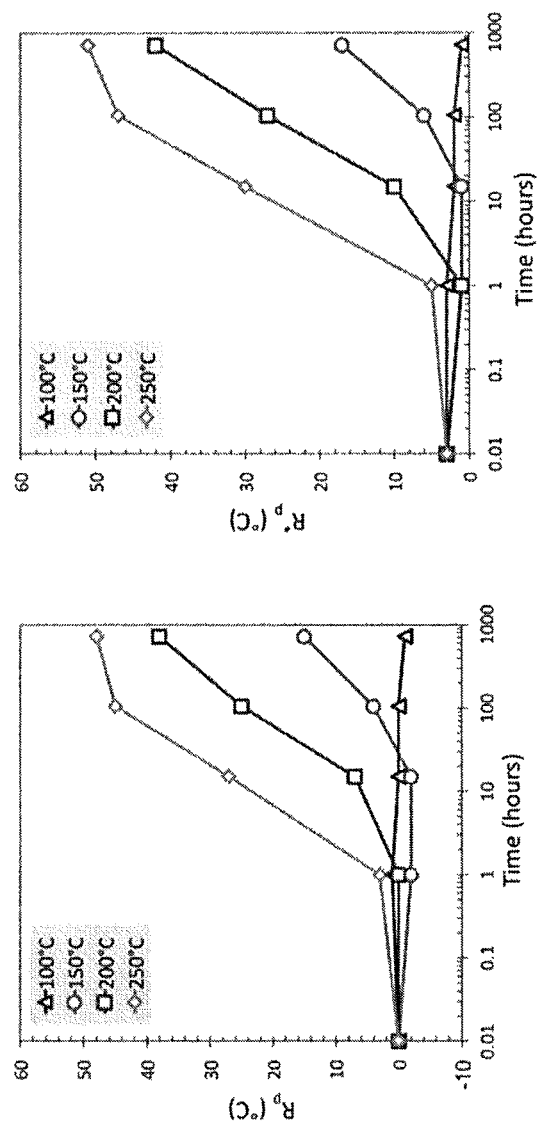
FIGS. 22A and 22B illustrate evolution of R-phase upon cooling (FIG. 22A) and heating (FIG. 22B) at various aging temperatures with exposure time.

FIGS. 21A and 21B summarize the evolution of Martensite formation to and reversion from its R-phase parent, and FIGS. 22A and 22B illustrate the changes in R-phase stability with respect to its parent, Austenite. Similar to the solution treated samples, initial aging shows clear suppression of both Martensite formation ($M_p$) and reversion ($M^*_p$), though this trend is reversed at the longer times and higher aging temperatures. It should be noted that the strength of the peak associated with Martensite formation appears to weaken as Martensite is suppressed (see, for example, the scan after aging 720 hours at 200° C.). This is a due to a combination of a weakening ΔH and a declining sensitivity in the DSC itself. Where the $M_p$ temperatures are difficult to pinpoint, the sensitivity was boosted and the peaks are identified with an inset graph.

We also observe that R-phase formation and reversion is not suppressed by aging and in fact appears to be stabilized (the R-phase formation ($R_p$) and reversion ($R^*_p$) peaks are moved upward.)

Figures 23A, 23B:
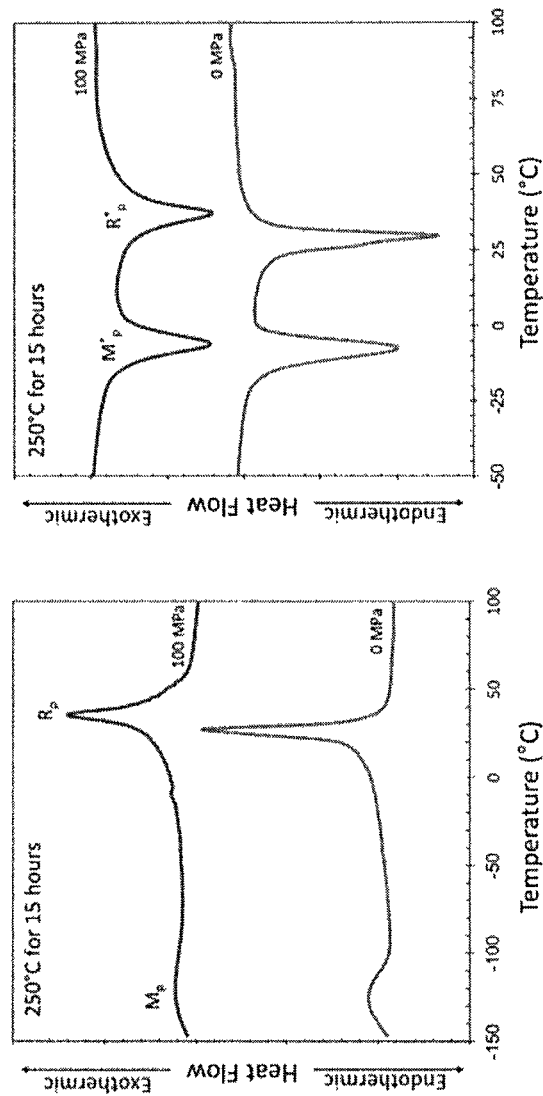
FIGS. 23A and 23B illustrate DSC graphs showing forward (FIG. 23A) and reverse (FIG. 23B) transformations after aging at 250° C. for 15 hours, with and without applied stress.
Figure 24A:
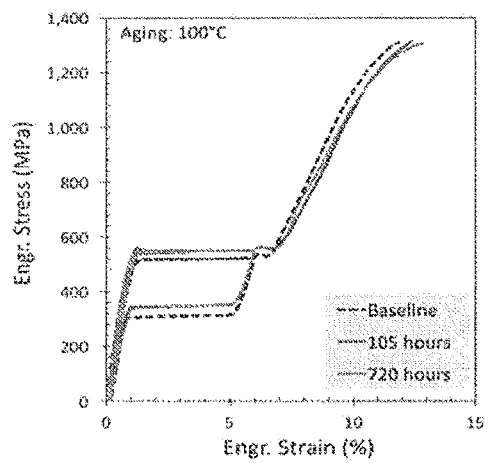
FIGS. 24A-24D illustrate tensile test results at 37° C. after aging at 100° C.
Figure 24B:
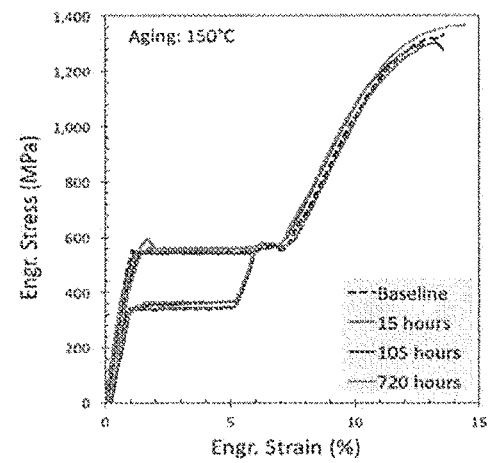
Figure 24C:
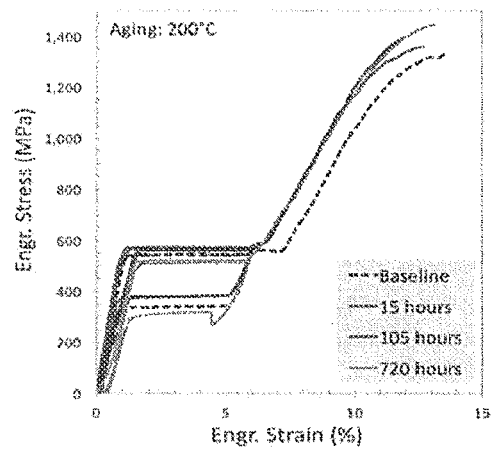
Figure 24D:
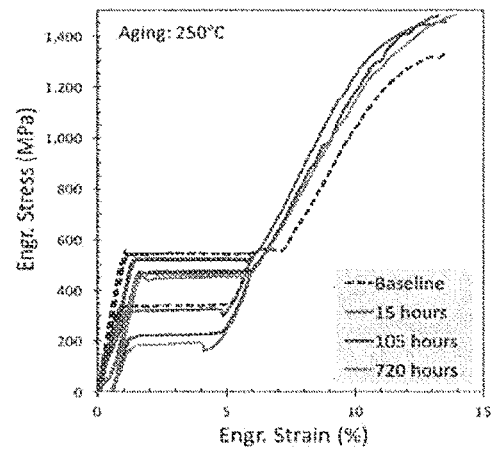

It is worth mentioning that aging can also be accelerated under stress. As an example, FIGS. 23A and 23B show that both Martensite and R-phase have evolved faster when stress of 100 MPa is applied during 250° C. treatment for 15 hours.

FIGS. 24A-24D show various tensile curves for all cold worked and aged conditions. At 100° C. and 150° C., a slight increase in plateau stresses is observed with exposure time, consistent with the suppression of Martensite transformation observed in DSC scans. Also, no changes in the ultimate tensile strength are observed at these lower aging temperatures, suggesting that the mechanism causing Martensite suppression does not produce significant strengthening.

Aging at 200° C. and 250° C. produces an initial increase in plateau heights followed by a decrease at longer aging times. The initial increase in plateau stresses is consistent with suppression of both Martensite formation and reversion temperatures, however the loss of stiffness at longer times appears to be inconsistent with the continued Martensite suppression indicated in the DSC results. In other words, transformation temperatures are declining, and so are the plateau heights, particularly the unloading plateau. This seeming contradiction will be a primary topic of discussion in the next section.

Turning now to a more in depth discussion of the experimental data and observations described above as well as in FIGS. 16-24. Aging, whether resulting in nickel clustering or the precipitation of $Ni_4Ti_3$, $Ni_3Ti_2$ or $Ni_2Ti$, enriches the NiTi matrix compound in titanium which in turn stabilizes B19' Martensite. Yet aging at very low temperatures appears to result in the opposite trend: a suppression of Martensite. This was shown in the solution treated case in which the parent phase is Austenite, as well as a cold-worked and aged condition in which the parent phase if the R-phase. This can be explained by the pinning effects that microstructural inhomogenieties have on Martensite. While stress inhomogenieties such as coherent precipitation or clustering will locally stabilize Martensite, they also bind to Martensite embryos, not allowing Martensite interfaces to advance. Ultimately, as precipitate coherency is lost and the intensity of the stress inhomogenieties is reduced, the effects of matrix composition dominate and transformation temperatures rise. These effects are just those observed in these studies.

Figures 25A, 25B:
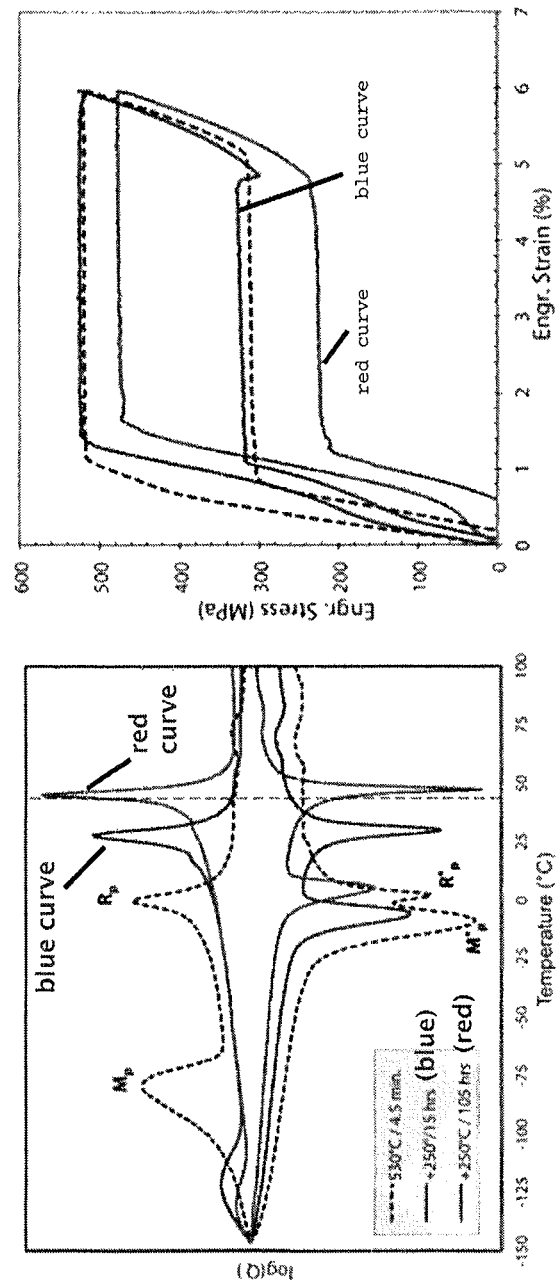
FIGS. 25A and 25B illustrate, respectively, the DSC and 37° C. tensile curves of the same wire heat treated three different ways, highlighting that plateaus are not dependent upon $A_f$.

Less clear, however, is the effect of aging on the stability of the R-phase with respect to its parent, Austenite. Because of the low Δε associated with the R-phase, one expects a much lower interaction with stress fields. The sharp increase in R and R* temperatures indicates that the R-phase too is stabilized by the titanium enrichment that occurs during the aging process. Lacking the elastic energy pinning effect, we see an immediate rise in R and R*, which results in a dramatic separation between R and M transformations. FIG. 25A, for example, in the blue curve, shows a separation upon cooling of 152° C. and 36° C. upon reversion. The red curve shows a separation upon cooling of 182° C. and 42° C. upon reversion. FIG. 25B highlights that the upper and lower stress plateaus are not dependent on $A_f$. Returning to FIG. 25A, we have three scenarios occurring during loading and unloading at 37° C.:

A to M upon loading and M to A upon unloading (dashed unaged curve),

A-to-R-to-M upon loading and M-to-R upon unloading (blue curve), and

R-to-M upon loading and M-to-R upon unloading (red curve)

Figure 26:
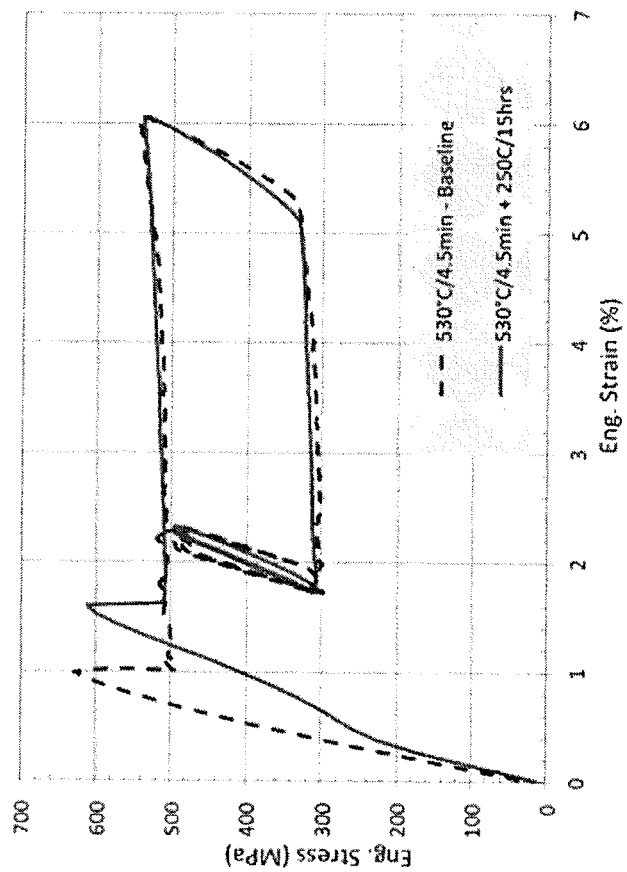
FIG. 26 illustrates a duty cycle comparison of A-M versus R-M superelasticity at 37° C. showing the difference in the duty cycle modulus after unloading and constraining on the lower plateau.

The last of these warrants discussion since we have quite satisfactory superelasticity at body temperature without the presence of Austenite (with $A_f$ greater than 37° C.). It remains unclear just what the advantages or disadvantages of such a condition are in practice. One could argue that the superelasticity is imperfect since unloading returns a twinned R-phase and thus a set of about 0.5%. But such an argument is flawed since this can easily be taken into account in the design of a product. More to the point is that the length of the plateau is shortened by 0.5% since $\Delta\varepsilon_{M-R}$ is less than $\Delta\varepsilon_{M-A}$—perhaps relevant to some products, though unlikely. On the other hand, one now has a mixture of R and M in a device constrained on the unloading plateau rather than a mixture of A and M, the former offering a lower modulus and greater ability to elastically accommodate a duty cycle without advancing Martensite interfaces. This, in turn, should lead to a more fatigue durable structure (see FIG. 26). This is an area requiring further exploration.

Figure 27:
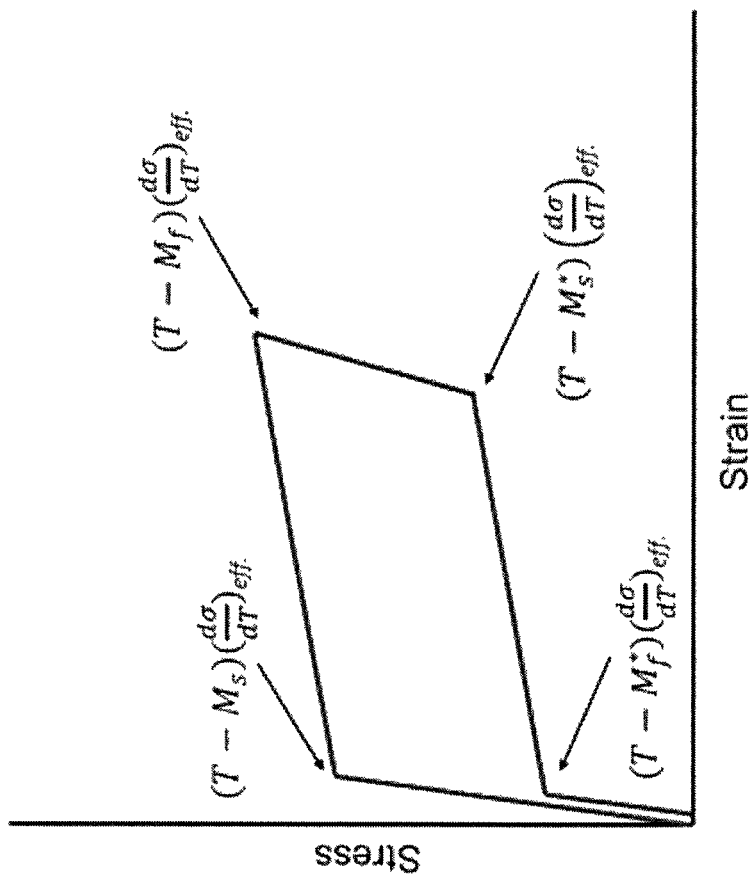
FIG. 27 illustrates a schematic of stress-strain behavior showing the relation between stress and transformation temperature.

Also of note are certain seeming discrepancies between the DSC traces and tensile properties. Again, this is highlighted by FIGS. 24A-24D in which we see a suppression of the thermal formation and reversion of Martensite, yet lower loading and unloading plateaus—aging for 105 hours at 250° C. makes it more difficult to thermally induce Martensite, yet easier to stress induce Martensite. These appear at first glance to be incongruous, but such is not the case. As illustrated in FIG. 27, plateau stresses are dictated by three factors:

The difference between ambient temperature and the relevant transformation temperature (for example, T-$M_s$ should reflect the start of the plateau).

The effective dσ/dT, or Clausius-Clapeyron coefficient, and

In some cases, strain localization, which can "cheat" the thermodynamics of the interfacial strain energy.

Figure 28C:
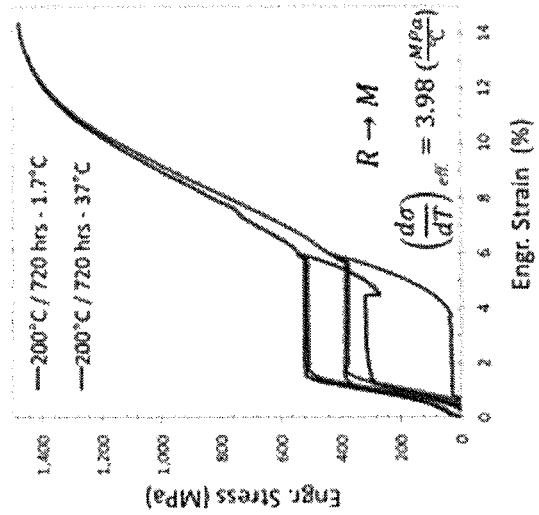
FIGS. 28A, 28B and 28C illustrate respective changes in $$\left(\frac{d\sigma}{dT}\right)_{\text{eff}}.$$
Figure 28B:
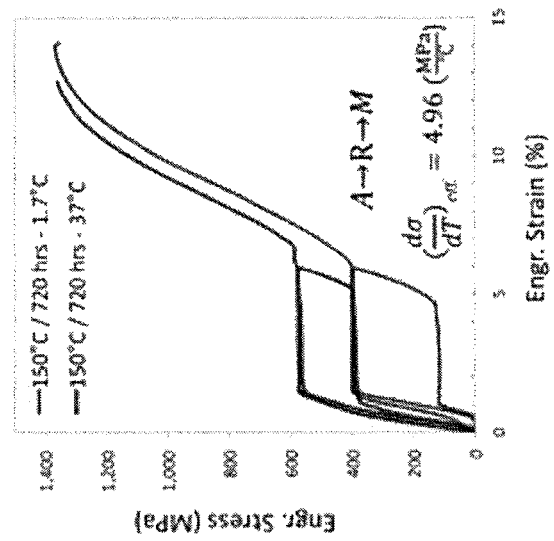
Figure 28A:
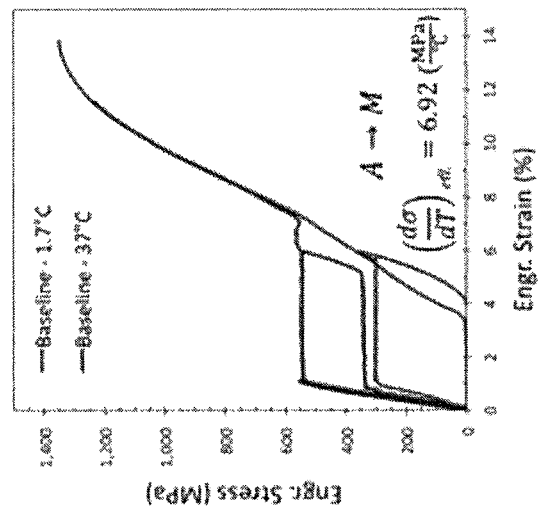

The first of these points is clear enough and can be easily observed via DSC, but the other two merit discussion. The Clausius-Clapeyron equation stipulates that dσ/dT=−ΔS/Δε, but there are three coefficients to consider: $(d\sigma/dT)_{A-R}$, $(d\sigma/dT)_{A-M}$, and $(d\sigma/dT)_{R-M}$, and where these three trajectories intersect on a stress-temperature phase diagram, there is a triple point. FIG. 27 uses the term $(d\sigma/dT)_{eff}$; when there is no R-phase, $(d\sigma/dT)_{eff}=(d\sigma/dT)_{A-M}$, when the triple point is above ambient temperature, $(d\sigma/dT)_{eff}=(d\sigma/dT)_{R-M}$ which is substantially lower. The most common case, however, is when the triple point lies between $M_p$ and ambient temperature, in which case $(d\sigma/dT)_{eff}$ is a weighted combination of $(d\sigma/dT)_{A-M}$ and $(d\sigma/dT)_{R-M}$. More detail on this construction is appreciated with reference to "The Measurement and Interpretation of Transformation Temperatures in Nitinol," by T. W. Duerig, A. R. Pelton and K. Bhattacharya, accepted for publication in Journal SMST (2017). Suffice it to say that as the R-phase is stabilized, the triple point increases in temperature, and we expect a decrease in the effective dσ/dT as increasing weight is placed on $(d\sigma/dT)_{R-M}$. To verify this, FIGS. 28A-28C show the $(d\sigma/dT)_{eff}$ for the three exemplary cases, and indeed we observe a marked decrease as R is stabilized, explaining why Martensite is becoming more difficult to thermally induce but easier to stress induce.

This brings us to perhaps the least studied aspect of translating transformation temperatures into plateau stresses: strain localization. Strain localization, or Lüders deformation, is a well-known yet oft ignored phenomenon in superelastic conditions exposed to uniaxial tension. In short, when the elastic influences of individual Martensite pockets impinge, they can reduce the total strain energy by coalescing into bands spanning across the entire cross section. This not only reduces the total interfacial area, it allows the volume fraction of Martensite to grow without further increases in strain energy. One often observes a drop in stress when the bands are formed, and then once formed, the plateaus are "perfectly" flat. In these cases, and in contrast to the idealization of FIG. 27, it is the $M_s$ temperature that is best associated with the plateau height. The same is observed when Martensite retreats, with a reverse yield drop and a flat unloading plateau.

The relevance of the above to what is observed here is exemplified by the longest of the aged conditions at 200° C. and 250° C. Here we begin to see a more pronounced reverse yield drop upon unloading, indicating that a great deal of strain energy is being relieved by the formation of bands. Since strain localization only occurs in the presence of tensile stresses, the same strain energy savings is not observed in a stress-free DSC test, so we expect unloading plateaus to be higher than those predicted by DSC. Thus as the thermal hysteresis increases as shown in FIG. 29, we expect greater energy savings through the formation of Lüders bands, and consequently higher unloading plateaus. While speculative, it is possible that the increase in hysteresis is due to the transition from coherent precipitates to semi-coherent, and finally to coherent.

As set forth above, it has been shown that Ni-rich Ti—Ni alloys are metastable even at temperatures as low as 100° C., both in the solution treated and quenched condition and in the cold worked and aged conditions typically used by the medical device industry. While the suppression in Martensite transformation temperatures and plateau stresses are not pronounced below 200° C., many medical devices specify transformation temperature ranges as tight as +/−3° C. Moreover, these temperatures are not uncommon in a host of processing operations such as co-extrusion and the application and curing of various coatings.

In addition to the suppression of Martensite, one observes a stabilization of the R-phase. This means the $R^*_f$ (or $A_f$) temperature can be increased even while Martensite reversion is suppressed and the unloading plateau lifted. The increased separation of the R and M transformations allows one to establish robust superelasticity at body temperature between the R and M phases, without the appearance of Austenite. As a result, these various new processing methods and resulting materials may advantageously provide one or more of the following advantages:

(a) a more compliant duty cycle with greater elastic range, and potentially greater displacement controlled durability;

(b) Exposures at temperatures≤150° C. resulted in stiffening of the material due to the suppression of Martensite formation ($M_p$) & reversion ($M^*_p$);

(c) Suppression of Martensite could be attributed to Ni clustering, precipitation, or the coherency of the precipitates OR a combination of all;

(d) Exposures at temperatures>150° C. resulted in loss of stiffness;

(e) Loss of stiffness is attributed to the decrease in dσ/dT due to stabilization of the R-phase;

(f) Stabilization of the R-phase at higher temperatures can also result in materials with an $A_f$ well above body temperature (i.e. 48° C.) with pseudoelasticity; however caution must be taken when exposing NiTi to temperatures<200° C. (e.g. when applying coatings).

Still further additional detail of the various embodiments described herein may be appreciated by reference to "The Measurement and Interpretation of Transformation Temperatures in Nitinol," by T. W. Duerig, A. R. Pelton and K. Bhattacharya, accepted for publication in Journal SMST (2017), the entirety of which is incorporated herein by reference for all purposes.

Any of the above variations of a superelastic medical component may be adapted for use in any of a wide variety of medical, biologic, neurological, combination stimulation and drug combination devices and that like as described and many others that would benefit from the advantages described herein. It is to be appreciated that cyclic loading as used herein along with corresponding alterations in design may be employed while still benefiting from the numerous advantages described herein.

Accordingly, any of the various embodiments described above can be adapted and configured for use in the field of interventional cardiology and neuroradiology. Exemplary non-limiting medical components can be one of an angioplasty balloon shaft, a stent, a stent graft, a coil or a component of a delivery system. Additionally or alternatively, the medical component can be adapted and configured for use in the field of cardiovascular surgery, general surgery or laparoscopic surgery. Exemplary non-limiting medical components can be one of a valve sizer, a tissue retractor, a heart valve, a stent for use in the arterial system, a stent for use in the venous system, an instrument or component of a specimen retrieval system. Additionally or alternatively the medical component can be adapted and configured for use in the field of orthopedic surgery, spine surgery or sports medicine. Exemplary non-limiting medical components can be one of a bone staple, a bone screw, a scoliosis rod, a spinal fixation rod, a suture retriever or a k-wire. Additionally or alternatively the medical component can be adapted and configured for use in the field of urology, gastrointestinal health, otolaryngology, obstetrics or gynecology. Exemplary non-limiting medical components can be one of a snare, a grasper, an esophageal stent, a biliary stent, a stent for use within the gut, or a sinus implant. Additionally or alternatively the medical component can be adapted and configured for use in the field of dentistry or orthodontics. Exemplary non-limiting medical components can be one of an arch wire, an orthodontic clip or a component used in a repair of the mouth. Exemplary non-limiting medical components can be adapted and configured for use as a diagnostic catheter, a therapeutic catheter, a stent, a needle, a wire localizer, an orthodontic arch wire, a lead for an implantable stimulation component or a component of an implantable drug delivery system.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the terms "patient-specific," "customized," and/or "adaptive," when used in reference to a glenoid implant or humeral implant, can be used interchangeably and can in some embodiments refer to the specialization of such features taking into consideration factors specific to a patient to be treated, including for example characteristics acquired from pre-operative analysis and planning or a selected reverse or anatomic shoulder procedure.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of processing a TiNi material to produce an implantable medical component, comprising:
    processing the TiNi material to produce a medical component by cold drawing, extruding or rolling, by aging heat treatments under stress in a range of 300° C. to 700° C. to achieve a desired shape of the implantable medical component and further aging at a temperature below 300° C. to produce a desired R-phase characteristic of depressing $M_p$ wherein the medical component has a stress free M*s below a normal body temperature, wherein a temperature separation of the stress free RP and Mp is at least 100° C.

2. The method of claim 1 wherein using use in-vivo at the normal body temperature the medical component contains at least some R-phase.

3. The method of claim 1 wherein a critical region of the medical component is substantially R-phase and Martensite.

4. The method of claim 3 wherein during a duty cycle applied during in-vivo use the medical component alternates between Martensite and R-phase.

5. The method of claim 1 wherein a temperature separation of the stress free R*p and M*p is at least 30° C.

6. The method of claim 1 wherein the TiNi material is a binary composition comprising Ti and Ni.

7. The method of claim 6 wherein the Ni atomic percentage is 50.5-51.5%.

8. The method of claim 1 wherein the TiNi material is a ternary composition comprising Ti and Ni and at least one other element.

9. The method of claim 1 wherein the TiNi material comprises more than 50% atomic Ni, from 0.1 to 3% of a Titanium substitution material with remaining composition comprising Ti wherein the Titanium substitution material is one of Hf, Zr, or Nb alone or in any combination.

* * * * *